(12) United States Patent
Birmingham et al.

(10) Patent No.: US 9,907,931 B2
(45) Date of Patent: Mar. 6, 2018

(54) ELASTIC INTRODUCER SHEATH

(71) Applicant: Medtronic, Inc., Minneapolis, MN (US)

(72) Inventors: Evelyn Birmingham, Ballybrit (IE); Niall Duffy, Ballybrit (IE); Ahmed M. Elmouelhi, Plymouth, MN (US); Patrick Griffin, Ballybrit (IE); Patrick Macaulay, Windsor, CA (US); John Milroy, Ballybrit (IE); Stephen J. Peter, San Rafael, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 251 days.

(21) Appl. No.: 14/260,537

(22) Filed: Apr. 24, 2014

(65) Prior Publication Data

US 2014/0236123 A1 Aug. 21, 2014

Related U.S. Application Data

(63) Continuation-in-part of application No. 13/791,110, filed on Mar. 8, 2013, now Pat. No. 9,192,751.

(60) Provisional application No. 61/719,360, filed on Oct. 26, 2012.

(51) Int. Cl.
*A61M 25/00* (2006.01)
*A61M 25/06* (2006.01)
*A61M 39/02* (2006.01)

(52) U.S. Cl.
CPC ...... *A61M 25/0023* (2013.01); *A61M 25/005* (2013.01); *A61M 25/0012* (2013.01); *A61M 25/0662* (2013.01); *A61M 39/0247* (2013.01); *A61M 25/0053* (2013.01);
(Continued)

(58) Field of Classification Search
CPC .......... A61M 25/0023; A61M 39/0247; A61M 2025/0687; A61M 2025/0024; A61M 2025/0025; A61M 2025/0681; A61M 2207/00; A61M 25/005; A61M 25/0012; A61M 25/0053; A61M 25/0054; A61M 25/0662; A61M 25/0014; A61M 25/0026; A61M 2039/1033; A61M 25/0034;
(Continued)

(56) References Cited

U.S. PATENT DOCUMENTS

| | | |
|---|---|---|
| 4,601,713 A | 7/1986 | Fuqua |
| 5,176,659 A | 1/1993 | Mancini |
| 5,322,519 A | 6/1994 | Ash |

(Continued)

FOREIGN PATENT DOCUMENTS

| | | |
|---|---|---|
| WO | WO 2004/037333 | 5/2004 |
| WO | WO 2010/075565 | 7/2010 |
| WO | WO 2011/035327 | 3/2011 |

OTHER PUBLICATIONS

International Search Report and Written Opinion for International Application No. PCT/US2013/063844, dated Jan. 3, 2014, 17 pages.

*Primary Examiner* — Jocelin Tanner
(74) *Attorney, Agent, or Firm* — Medler Ferro Woodhouse & Mills PLLC

(57) ABSTRACT

An elastic percutaneous elastic introducer sheath is disclosed which can locally expand and reduce to accommodate a transcatheter medical device. The elastic introducer sheath includes a non-circumferentially continuous elastic frame, a liner, and a jacket.

20 Claims, 31 Drawing Sheets

(52) U.S. Cl.
CPC ............... *A61M 2025/0024* (2013.01); *A61M 2025/0687* (2013.01); *A61M 2207/00* (2013.01); *Y10T 29/49826* (2015.01)

(58) Field of Classification Search
CPC ........... A61M 25/0032; A61M 25/0052; Y10T 29/49826; A61B 17/3439; A61B 17/3431; A61F 2/93
See application file for complete search history.

(56) References Cited

U.S. PATENT DOCUMENTS

| | | | |
|---|---|---|---|
| 5,447,503 A | 9/1995 | Miller | |
| 5,458,573 A | 10/1995 | Summers | |
| 5,472,428 A | 12/1995 | Peters | |
| 5,549,662 A * | 8/1996 | Fordenbacher | A61F 2/93 606/198 |
| 5,573,508 A | 11/1996 | Thornton | |
| 5,718,693 A | 2/1998 | Gupta | |
| 5,762,604 A | 6/1998 | Kicturakis | |
| 5,772,628 A | 6/1998 | Bacich et al. | |
| 5,797,951 A | 8/1998 | Mueller | |
| 5,810,776 A | 9/1998 | Bacich et al. | |
| 5,824,046 A | 10/1998 | Smith et al. | |
| 5,911,702 A | 6/1999 | Romley et al. | |
| 5,935,122 A * | 8/1999 | Fourkas | A61B 17/3462 604/249 |
| 5,997,508 A | 12/1999 | Lunn et al. | |
| 6,090,072 A | 7/2000 | Kratoska et al. | |
| 6,183,443 B1 | 2/2001 | Kratoska et al. | |
| 6,197,016 B1 | 3/2001 | Fourkas et al. | |
| 6,312,443 B1 * | 11/2001 | Stone | A61B 17/025 606/198 |
| 6,325,812 B1 | 12/2001 | Dubrul et al. | |
| 6,425,908 B2 | 7/2002 | Ravenscroft et al. | |
| 6,428,566 B1 | 8/2002 | Holt | |
| 6,749,600 B1 | 6/2004 | Levy | |
| 6,808,520 B1 | 10/2004 | Fourkas et al. | |
| 6,814,715 B2 | 11/2004 | Bonutti et al. | |
| 7,090,688 B2 | 8/2006 | Nishtala et al. | |
| 7,144,386 B2 | 12/2006 | Korkor et al. | |
| 7,172,620 B2 | 2/2007 | Gilson | |
| 7,192,433 B2 | 3/2007 | Osypka et al. | |
| 7,329,268 B2 | 2/2008 | Van Nguyen et al. | |
| 7,338,518 B2 | 3/2008 | Chobotov | |
| 7,476,232 B2 | 1/2009 | Deal | |
| 7,524,305 B2 | 4/2009 | Moyer | |
| 7,534,250 B2 | 5/2009 | Schaeffer et al. | |
| 7,591,832 B2 | 9/2009 | Eversull et al. | |
| 7,637,893 B2 | 12/2009 | Christensen et al. | |
| 7,699,864 B2 | 4/2010 | Kick et al. | |
| 7,713,193 B2 | 5/2010 | Nance et al. | |
| 7,736,299 B2 | 6/2010 | Klenk et al. | |
| 7,762,995 B2 | 7/2010 | Eversull et al. | |
| 7,766,820 B2 | 8/2010 | Core | |
| 7,780,630 B2 | 8/2010 | Jenson et al. | |
| 7,780,692 B2 | 8/2010 | Nance et al. | |
| 7,879,024 B2 | 2/2011 | Thorstenson et al. | |
| 7,887,733 B2 | 2/2011 | Moyer | |
| 7,892,203 B2 | 2/2011 | Lenker et al. | |
| 7,896,897 B2 | 3/2011 | Gresham et al. | |
| 7,909,798 B2 | 3/2011 | Osypka | |
| 7,927,309 B2 | 4/2011 | Palm | |
| 7,951,110 B2 | 5/2011 | Bishop et al. | |
| 7,963,952 B2 | 6/2011 | Wright, Jr. et al. | |
| 7,967,798 B2 | 6/2011 | Reydel et al. | |
| 7,985,228 B2 | 7/2011 | Phan et al. | |
| 7,985,232 B2 | 7/2011 | Potter et al. | |
| 7,993,350 B2 | 8/2011 | Ventura et al. | |
| 8,034,072 B2 | 10/2011 | Nguyen et al. | |
| 8,092,481 B2 | 1/2012 | Nance et al. | |
| 8,414,645 B2 | 4/2013 | Dwork et al. | |
| 2002/0099431 A1 | 7/2002 | Armstrong et al. | |
| 2005/0070881 A1 * | 3/2005 | Gribbons | A61M 25/0052 604/525 |
| 2005/0113804 A1 | 5/2005 | von Lehe et al. | |
| 2006/0015171 A1 | 1/2006 | Armstrong | |
| 2006/0052750 A1 | 3/2006 | Lenker et al. | |
| 2006/0074478 A1 | 4/2006 | Feller, III | |
| 2006/0111649 A1 * | 5/2006 | Zhou | A61M 25/0012 600/585 |
| 2006/0265056 A1 | 11/2006 | Nguyen et al. | |
| 2007/0167930 A1 * | 7/2007 | Eversull | A61M 25/0668 604/524 |
| 2007/0239266 A1 | 10/2007 | Birdsall | |
| 2007/0239269 A1 | 10/2007 | Dolan et al. | |
| 2008/0065011 A1 | 3/2008 | Marchand et al. | |
| 2008/0188928 A1 * | 8/2008 | Salahieh | A61M 25/0054 623/2.11 |
| 2008/0243072 A1 | 10/2008 | Jensen et al. | |
| 2010/0082000 A1 * | 4/2010 | Honeck | A61M 25/0045 604/246 |
| 2010/0094392 A1 * | 4/2010 | Nguyen | A61F 2/2427 623/1.11 |
| 2011/0251681 A1 | 10/2011 | Shipley et al. | |
| 2012/0083877 A1 | 4/2012 | Nguyen et al. | |
| 2012/0158033 A1 | 6/2012 | Deal | |
| 2014/0012281 A1 * | 1/2014 | Wang | A61M 25/0023 606/108 |

\* cited by examiner

ELASTIC INTRODUCER SHEATH

CROSS-REFERENCE TO RELATED APPLICATION

This application claims benefit under 35 U.S.C. 119(e) to U.S. Provisional Patent Application 61/719,360, filed Oct. 26, 2012, which is incorporated by reference herein in its entirety. This application is also a continuation-in-part of U.S. Non-Provisional application Ser. No. 13/791,110, filed Mar. 8, 2013, which is incorporated by reference herein in its entirety.

BACKGROUND

Field of the Disclosure

The present invention is related to percutaneous introducer sheaths, in particular a percutaneous elastic introducer sheath designed to introduce a transcatheter device into a patient's vasculature. The percutaneous elastic introducer sheath can accommodate the delivery of transcatheter devices of a range of sizes.

Background Art

A percutaneous introducer sheath is used to access the vascular system of a patient and acts as a way to introduce and position various transcatheter medical devices within the patient. The introducer sheath is a tube-like member which is partially inserted into the vasculature at a puncture site, typically in either the femoral, brachial, or radial artery of the patient. The proximal, or working end, of the introducer sheath is accessible outside of the vasculature for the introduction of transcatheter medical devices through the sheath. A guide wire can be inserted through the introducer sheath and subsequently steered through the vascular system to the site of therapy.

A typical introducer sheath system contains an access lumen for introduction of transcatheter medical devices, a Luer hub for connection to syringes and other peripheral devices, and a hemostasis valve to prevent blood loss from the lumen of the introducer sheath.

Large-profile transcatheter medical devices have traditionally required a larger-profile introducer sheath which provides a fixed internal clearance to allow the device to pass through the patient's vasculature. Such procedures using the large-profile transcatheter medical devices, typically through the femoral artery, are therefore limited to patients with sufficient vessel size to accommodate the introducer sheath. In order to extend the availability of large-profile transcatheter devices to patients with smaller vessel sizes, an introducer with a smaller profile that locally expands within the patient's vasculature to allow passage of the large-profile transcatheter device is desired. Local expansion and subsequent recoil of the elastic introducer profile is less traumatic on the patient's vessel than a sustained expansion for a large-profile introducer sheath.

BRIEF SUMMARY

Provided herein is an elastic percutaneous introducer sheath that generally includes a liner, an elastic frame, and a jacket having a longitudinal gap. The elastic introducer can be locally expanded once in situ and can elastically recoil to a reduced diameter. The elastic frame within the introducer allows expansion of the introducer, especially when passing the largest part of the transcatheter medical device being introduced. By use of the elastic frame, only the part of the introducer with the largest portion of the device is expanded. Once the transcatheter device is passed, the elastic frame acts as a spring to fully or partially collapse the diameter of the introducer.

In view thereof, disclosed herein are aspects of an elastic surgical access device including a circumferentially continuous biocompatible material layer, an elastic frame, and a non-circumferentially continuous biocompatible material layer connected to the elastic frame and to the circumferentially continuous biocompatible material layer, the non-circumferentially continuous biocompatible material layer having a longitudinal gap in an expanded configuration.

In another exemplary embodiment, disclosed herein are aspects of a locally expandable surgical access device including a non-circumferentially continuous biocompatible material layer having a longitudinal gap along a length of the access device, a circumferentially continuous biocompatible material layer connected to the non-circumferentially continuous biocompatible material layer, and an elastic frame extending across the longitudinal gap connected to the non-circumferentially continuous biocompatible material layer.

In another exemplary embodiment, disclosed herein are aspects of a method for percutaneously introducing a medical device into a patient's body including providing an elastic material sheet, cutting an elastic frame from the elastic material sheet, attaching a non-circumferentially continuous biocompatible material layer to the elastic frame, and attaching a circumferentially continuous biocompatible material layer to the non-circumferentially continuous biocompatible material later.

BRIEF DESCRIPTION OF THE DRAWINGS/FIGURES

The accompanying figures, which are incorporated herein, form part of the specification and illustrate embodiments of an elastic surgical access device. Together with the description, the figures further serve to explain the principles of and to enable a person skilled in the relevant art(s) to make and use the elastic surgical access device described herein. In the drawings, like reference numbers indicate identical or functionally similar elements.

DETAILED DESCRIPTION

Figure 1:
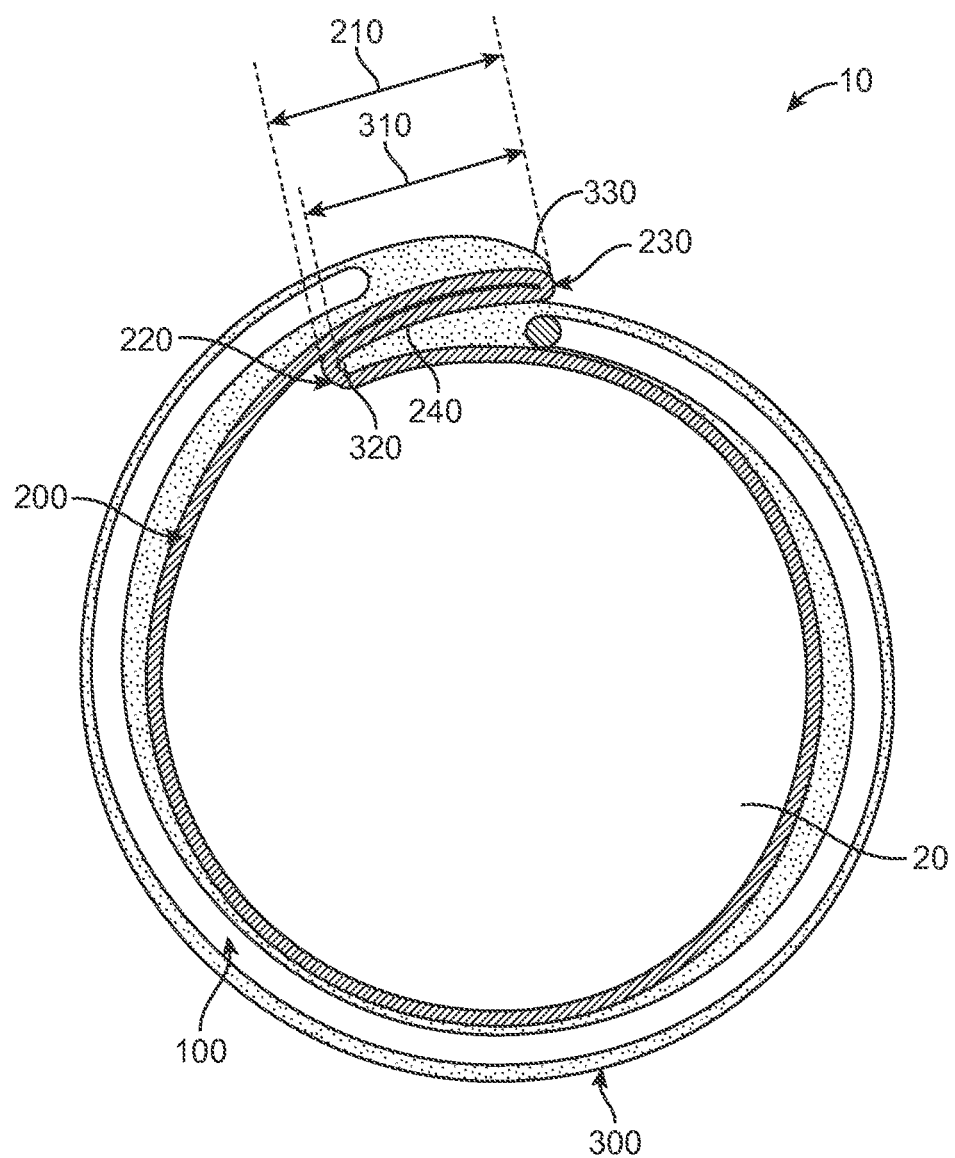
FIG. 1 is a sectional view of an elastic introducer according to an aspect of this disclosure.

The following detailed description of an elastic surgical access device refers to the accompanying figures that illustrate exemplary embodiments. Other embodiments are possible. Modifications can be made to the embodiments described herein without departing from the spirit and scope of the present invention. Therefore, the following detailed description is not meant to be limiting.

Referring to FIGS. 1 and 14-17, introducer system 1 includes an elastic introducer 10 that has a proximal end 12 and a distal end 14. Elastic introducer 10 includes a wire structure 100, a liner 200, and a jacket 300. In one aspect, wire structure 100 is laminated between liner 200 and jacket 300. In an alternate aspect, wire structure 100 is embedded within jacket 300. Wire structure 100 provides kink resistance for elastic introducer 10 and also allows elastic introducer 10 to actively recoil to a reduced diameter after passage of a transcatheter medical device through a portion of elastic introducer 10. Elastic introducer 10 includes a full diameter section 70 adjacent to hub 15 at proximal end 12. In full diameter section 70, wire structure 100 is coiled. In full diameter section 70, jacket 200 and liner 300 are circumferentially continuous and concentric with coiled wire structure 101. Elastic introducer 10 also includes an expandable transition section 80 and an expandable section 90. Expandable transition section 80 tapers the diameter of elastic introducer 10 from full diameter section 70 to expandable section 90. In expandable transition section 80 and expandable section 90, wire structure 100 is bent around a longitudinal axis into a C-shaped wire structure 103 forming a series of non-continuous circumferential loops. In one aspect, jacket 300 and C-shaped wire structure 103 are not circumferentially continuous in expandable transition section 80 and expandable section 90 and include a longitudinal gap visible in an expanded configuration. Expandable transition section 80 facilitates a smooth transition from hub 15 and full diameter section 70 to expandable section 90.

Typically, elastic introducer 10 is inserted into a vessel, such as the femoral artery, passing through the skin of a patient, such that the distal end 14 of elastic introducer 10 is inserted into the vessel. In one aspect, elastic introducer 10 includes a tapered tip for insertion through the vessel wall without roll back of the tip. Elastic introducer 10 can also include a suture eyelet for suture attachment to tissue. In a further aspect, elastic introducer 10 can be used with a guide wire. In one aspect, elastic introducer 10 can be compatible with a 0.035 inch guide wire.

Figure 9:
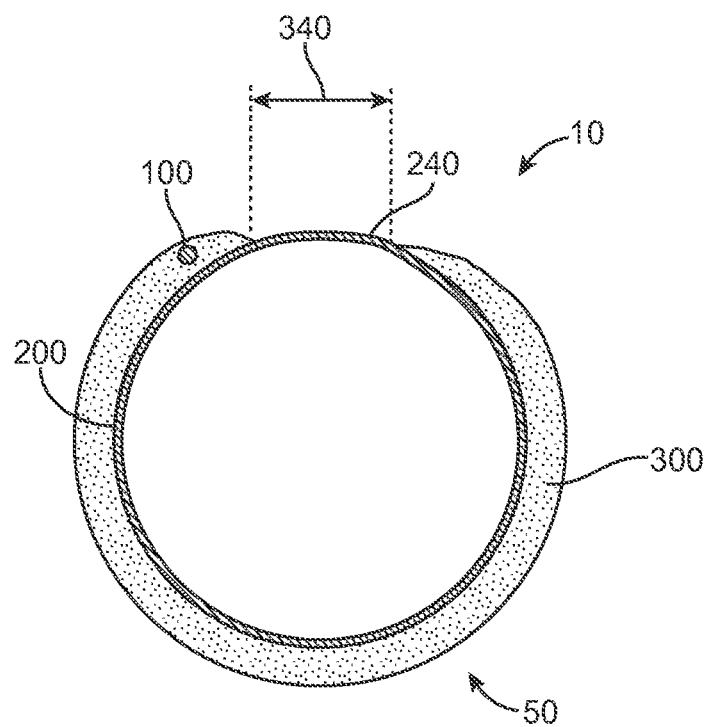
FIG. 9 is a sectional view of an elastic introducer according to an aspect of this disclosure.
Figure 10:
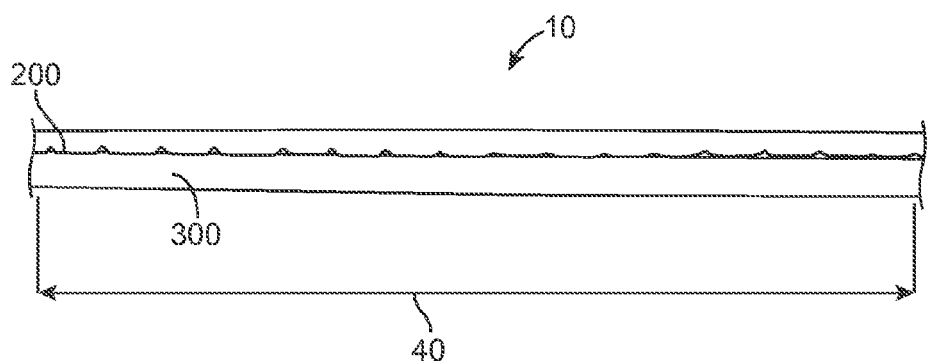
FIG. 10 is a top view of an elastic introducer according to an aspect of this disclosure.
Figure 11:
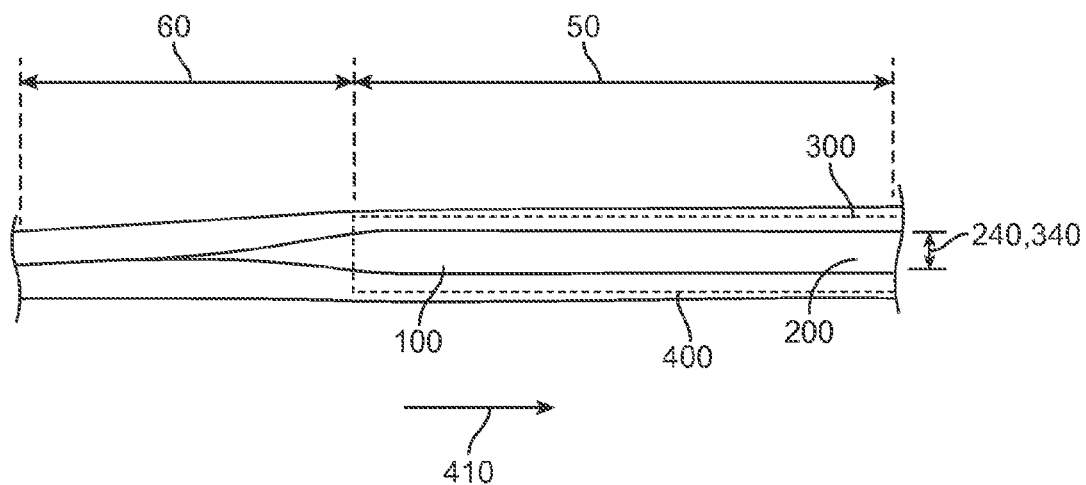
FIG. 11 is a top view of an elastic introducer according to an aspect of this disclosure.
Figure 12:
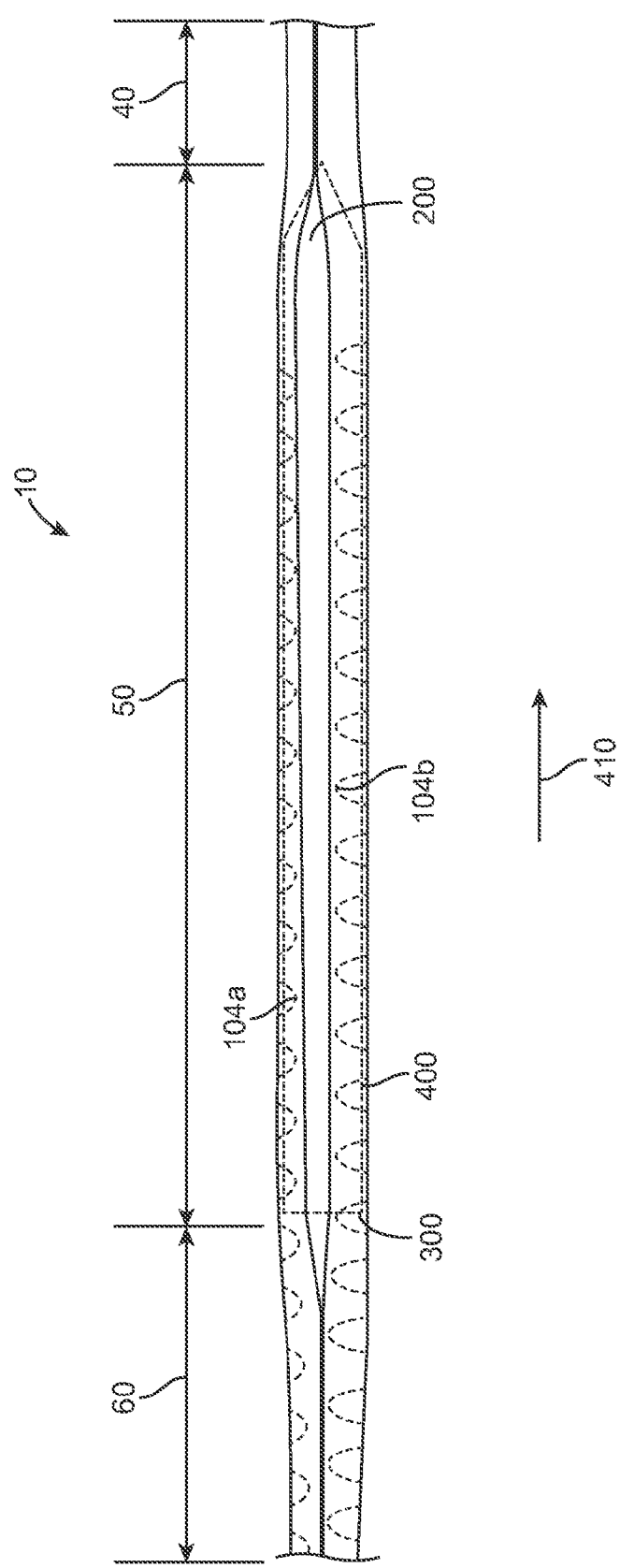
FIG. 12 is a top view of an elastic introducer according to an aspect of this disclosure.
Figure 13:
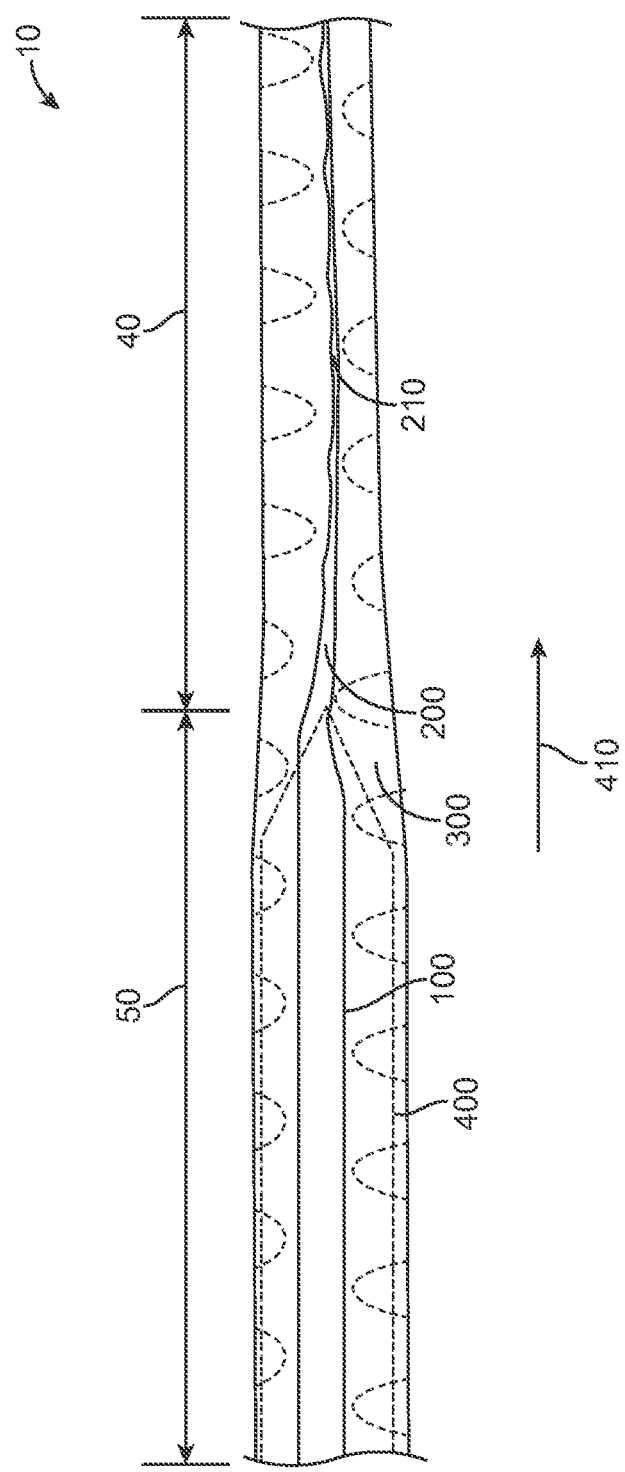
FIG. 13 is a top view of an elastic introducer according to an aspect of this disclosure.
Figure 14:
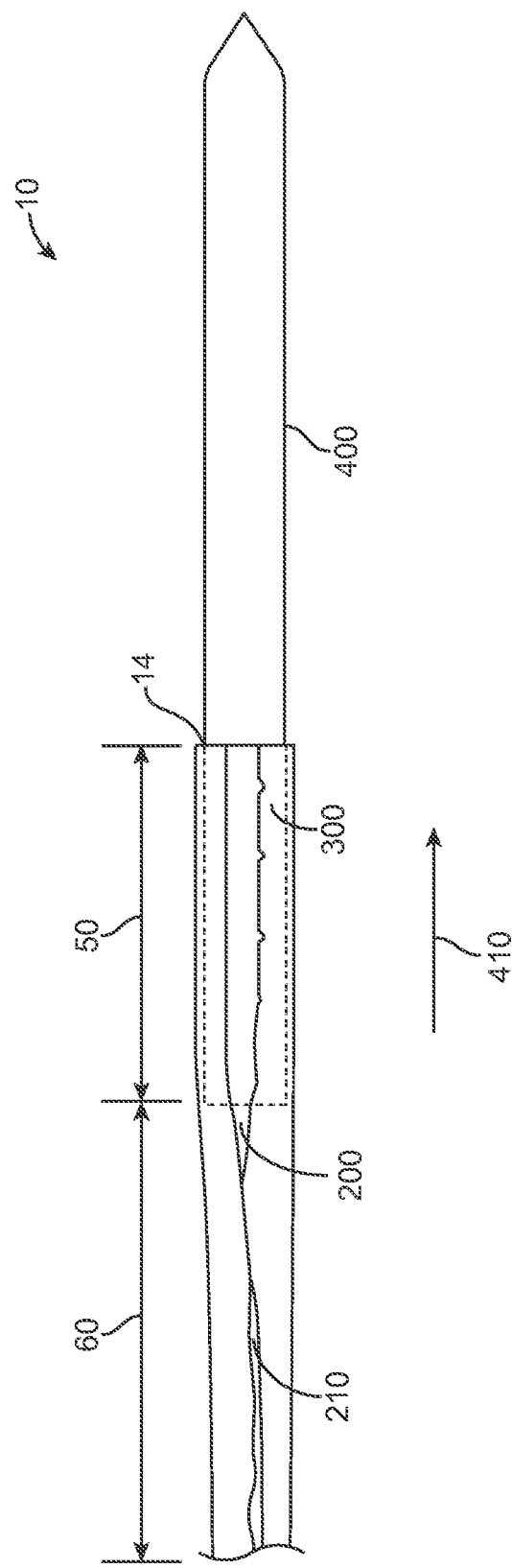
FIG. 14 is a top view of an elastic introducer according to an aspect of this disclosure.
Figure 16:
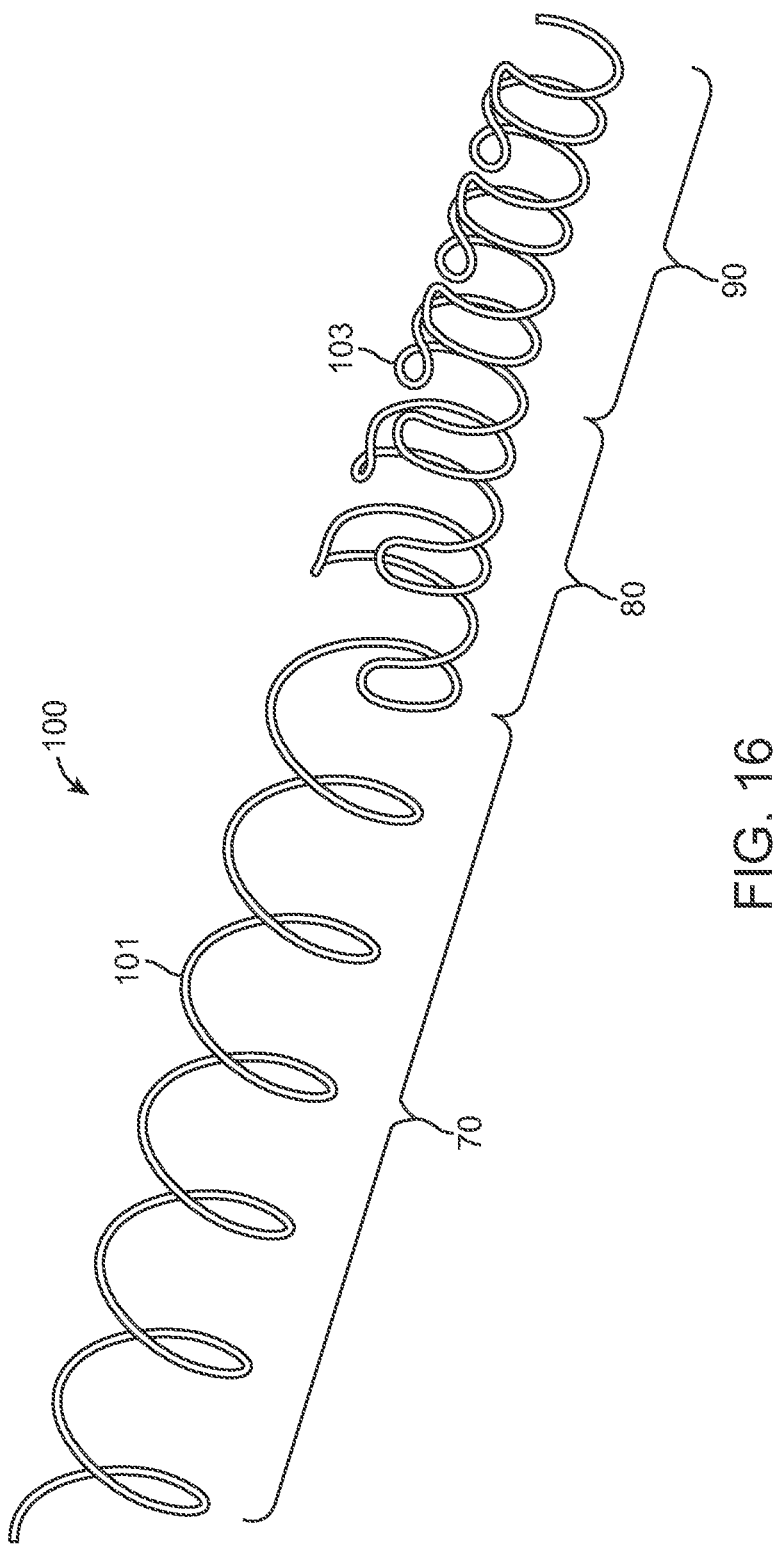
FIG. 16 is a perspective view of a wire structure of an elastic introducer according to an aspect of the disclosure.
Figure 17:
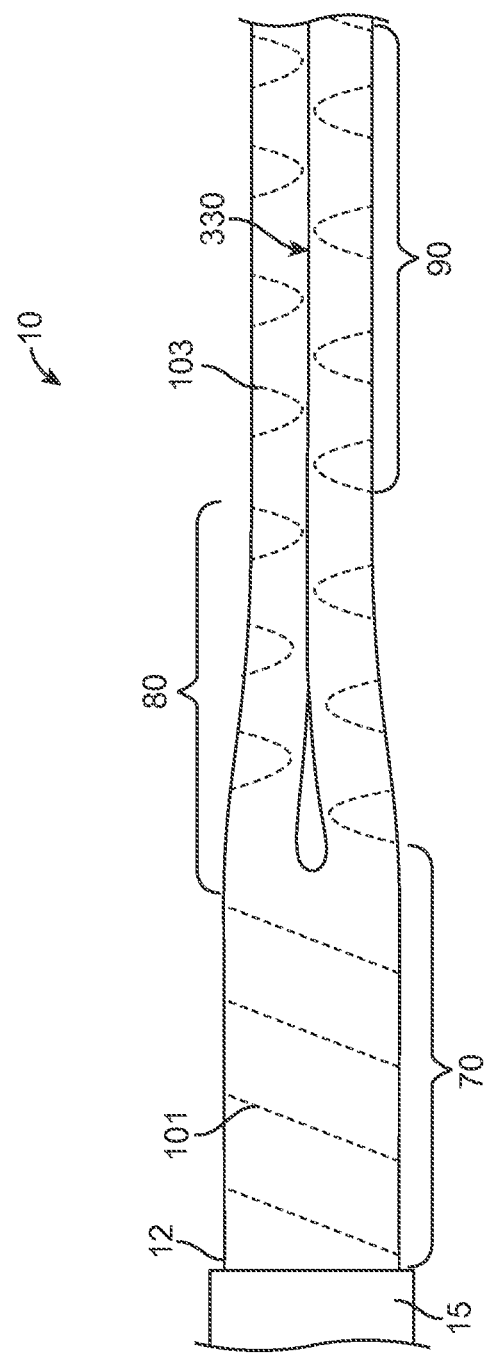
FIG. 17 is a top view of an elastic introducer according to an aspect of this disclosure.

In one aspect, liner 200 is circumferentially continuous and forms a lumen 20. In this aspect, wire structure 100 and jacket 300 are not circumferentially continuous and include a longitudinal gap visible in an expanded configuration. As shown in FIGS. 1 and 16-17, in a collapsed configuration, elastic introducer 10 includes a liner overlap region 210 and a jacket overlap region 310 in expandable transition section 80 and expandable section 90. Liner overlap region 210 includes liner gap portion 240 defined by an inner fold 220 and an outer fold 230 of liner 200. Liner gap portion 240 can be at least partially covered by jacket 300. In one aspect, liner 200 extends around inner edge 320 to form inner fold 220. Jacket overlap region 310 is defined by inner edge 320 and outer edge 330 of jacket 300. In an expanded configuration, inner edge 320 and outer edge 330 are separated longitudinally to form a jacket gap 340 (FIG. 9). In such a configuration, inner fold 220 and outer fold 230 are flattened to allow liner gap portion 240 to extend across jacket gap 340.

In one aspect, liner 200 is tetrafluoroethylene (TFE). In alternate aspects, liner 200 can be Teflon®, polytetrafluoroethylene (PTFE), polyethylene, polyethylene terephthalate (PET), or polyester. Liner 200 can have a low coefficient of friction on its inner surface to facilitate advancement of a transcatheter medical device through the elastic introducer 10.

In one aspect, jacket 300 is polyurethane (e.g. Pellethane®, Elasthane™, Texin®, or Tecothane®) and can include 20% barium sulfate added as a radipacifier. In alternate aspects, jacket 300 can be a polyamide polyether block copolymer such as Pebax®, nylon 12, or polyethylene. The material for jacket 300 can also be loaded with tungsten or bismuth subcarbonate to add radiopacity so that elastic introducer 10 can be radio detectable (radiopaque).

Wire structure 100 can be nickel titanium, Nitinol, with the diameter of the wire ranging from approximately 0.005 inches to approximately 0.02 inches. In alternate aspects, wire structure 100 can be nickel-cobalt-chromium-molybdenum (MP35N), stainless steel, high spring temper steel, or any other metal or composite having elastic properties to permit extension and recoil of elastic introducer 10.

Figure 2:
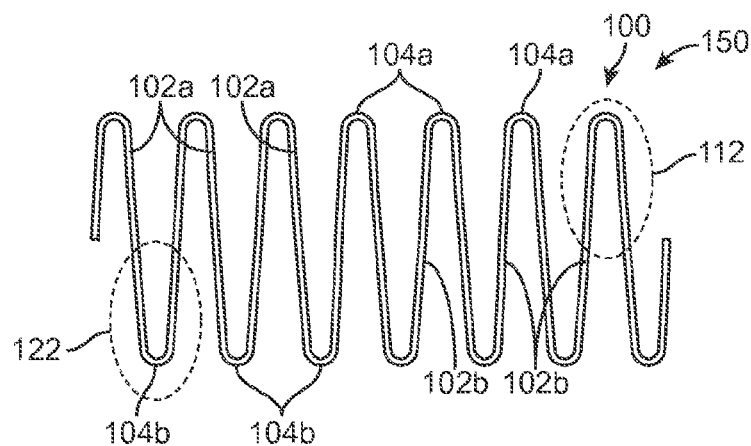
FIG. 2 is a front view of a wire structure of an elastic introducer according to an aspect of this disclosure.
Figure 3:
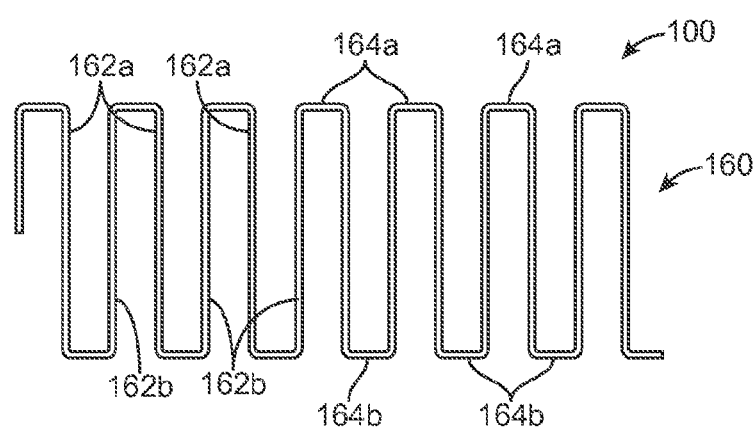
FIG. 3 is a front view of a wire structure of an elastic introducer according to an aspect of this disclosure.
Figure 4:
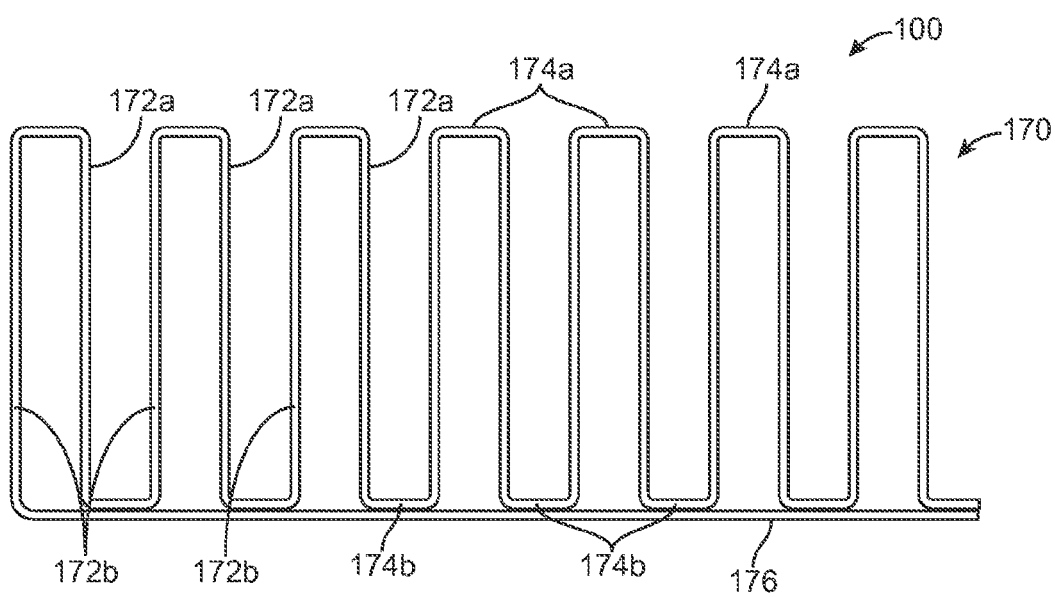
FIG. 4 is a front view of a wire structure of an elastic introducer according to an aspect of this disclosure.

Referring now to FIGS. 2-4, wire structure 100 includes a repeating longitudinal pattern and is shown in a flat or uncurved state. For example, wire structure 100 can include a sinusoid pattern 150 (FIG. 2), a square pattern 160 (FIG. 3), or a modified square pattern 170 including a spine 176 (FIG. 4). Sinusoid pattern 150 includes a series of alternating adjacent straight portions 102a and 102b. Each straight portion 102a is joined to a first adjacent straight portion 102b by a first bent end portion 104a and to a second adjacent straight portion 102b by a second bent end portion 104b. Conversely, each straight portion 102b is joined to two straight portions 102a by first bent end portion 104a and second bent end portion 104b.

Square pattern 160 includes a series of alternating adjacent straight portions 162a and 162b. Each straight portion 162a is joined to a first adjacent straight portion 162b by a first end portion 164a and to a second adjacent straight portion 162b by a second end portion 164b. Conversely, each straight portion 162b is joined to two straight portions 162a by first end portion 164a and second end portion 164b.

Modified square pattern 170 includes a series of alternating adjacent straight portions 172a and 172b. Each straight portion 172a is joined to a first adjacent straight portion 172b by a first end portion 174a and to a second adjacent straight portion 172b by a second end portion 174b. Conversely, each straight portion 172b is joined to two straight portions 172a by first end portion 174a and second end portion 174b. Spine 176 extends along end portions 174b. Spine 176 adds additional tensile rigidity to wire structure 100. In a further aspect, end portions 174b adjacent spine 176 can be welded or otherwise fixed to spine 176.

The below discussion refers to sinusoidal portion 150 of wire structure 100, however square pattern 160 or modified square pattern 170 could also be used for wire structure 100.

Figure 5:
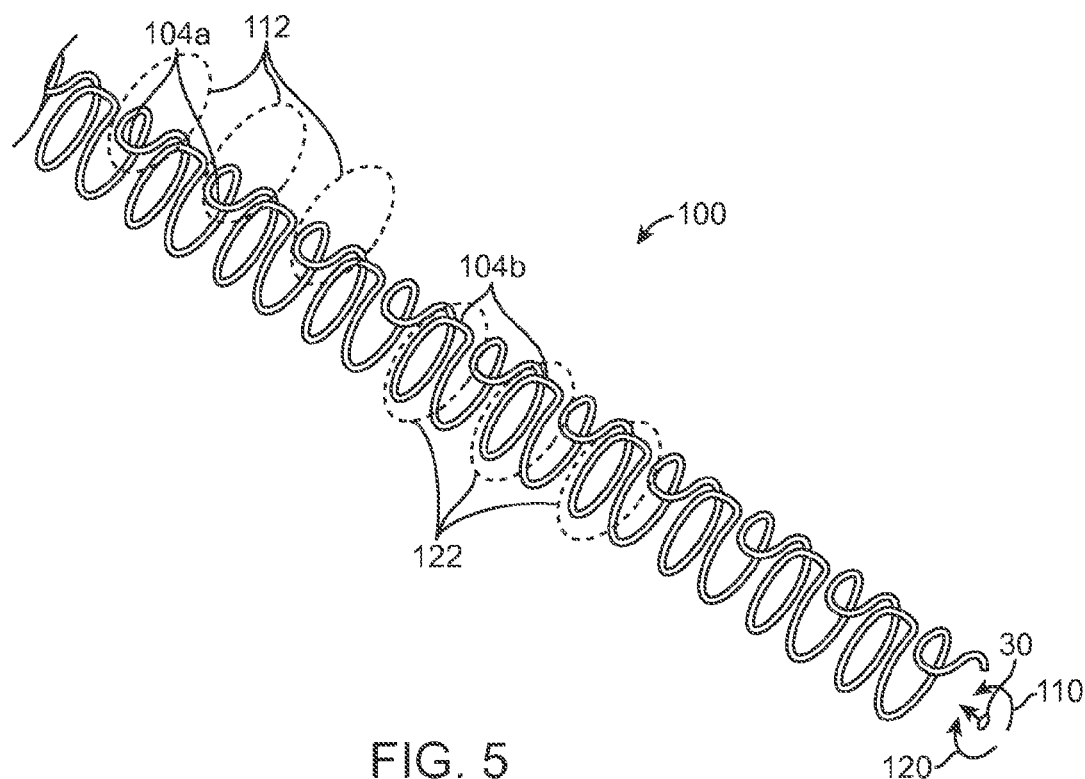
FIG. 5 is a perspective view of a wire structure of an elastic introducer according to an aspect of the disclosure.
Figure 6:
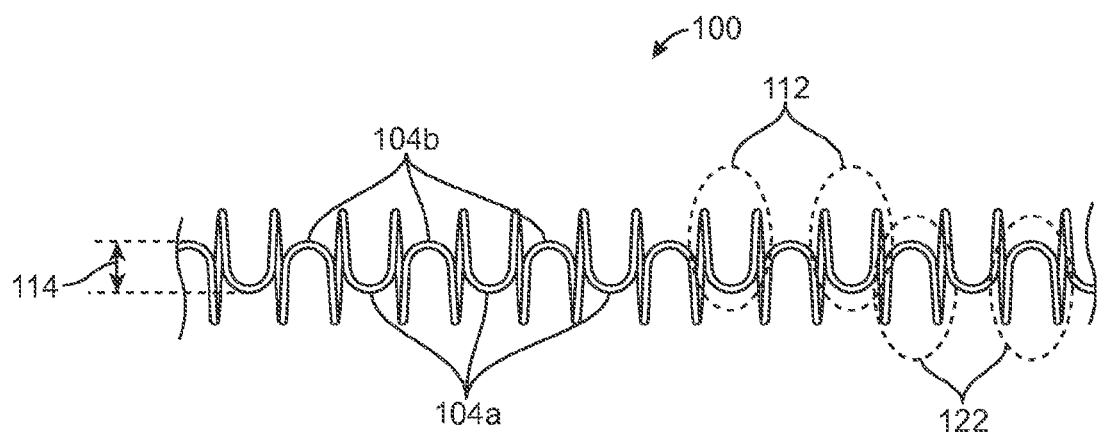
FIG. 6 is a top view of a wire structure of an elastic introducer according to an aspect of this disclosure.

Referring now to FIGS. 5-6, along the length of elastic introducer 10, the straight portions of wire structure 100 are curved about longitudinal axis 30 into a C-shaped wire structure 103 forming a series of non-continuous circumferential loops. To form the non-continuous circumferential loops, a first loop portion 112 of straight portions 102a and 102b joined by first bent end portion 104a is curved in a first radial direction 110. A second loop portion 122 of straight portions 102a and 102b joined by second bent end portion 104b is curved in a second radial direction 120. First loop portions 112 and second loop portions 122 form a series of alternating non-continuous circumferential loops extending along longitudinal axis 30. In one aspect, in a collapsed configuration of elastic introducer 10, first loop portions 112 and second loop portions 122 overlap longitudinally as demonstrated by wire overlap region 114. In one aspect, when elastic introducer 10 is in a collapsed configuration, first loop portions 112 are positioned within second loop portions 122 in wire overlap region 114 such that the second loop portions 122 cover the first loop portions 112. In an alternate aspect, when elastic introducer 10 is in a collapsed configuration, first loop portions 112 and second loop portions 122 do not overlap and do not include a wire overlap region 114.

Figure 7:
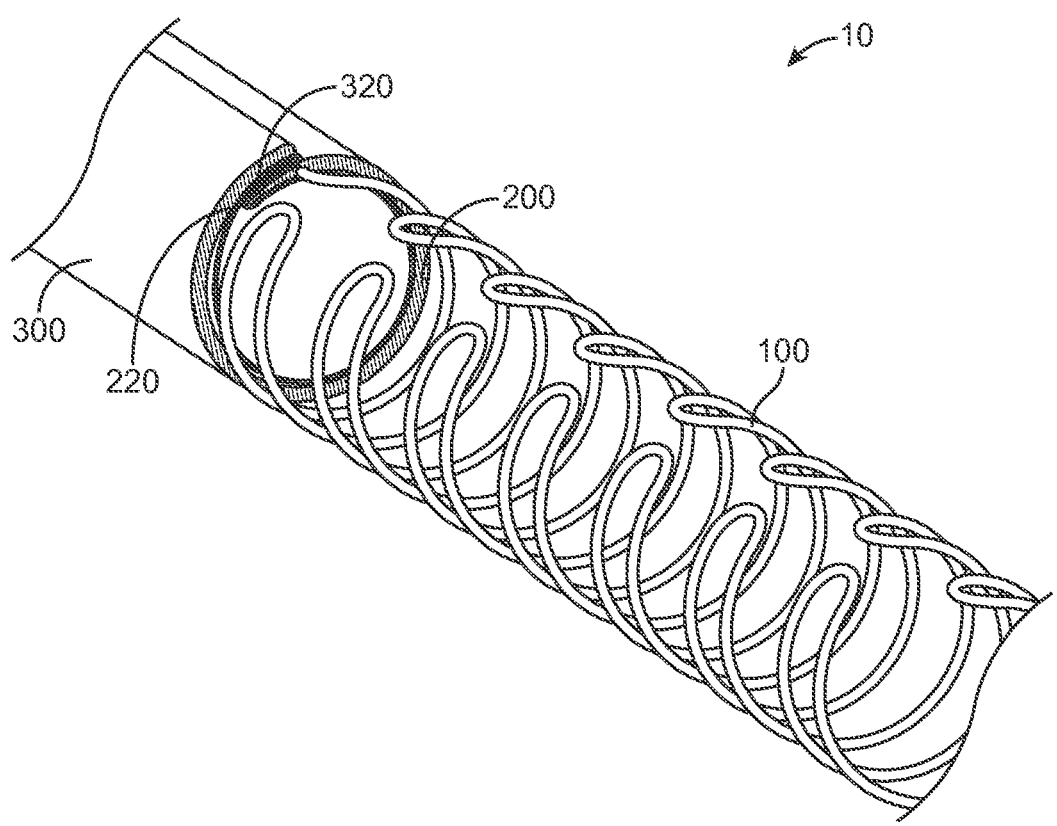
FIG. 7 is a perspective and cut away view of an elastic introducer according to an aspect of this disclosure.
Figure 8:
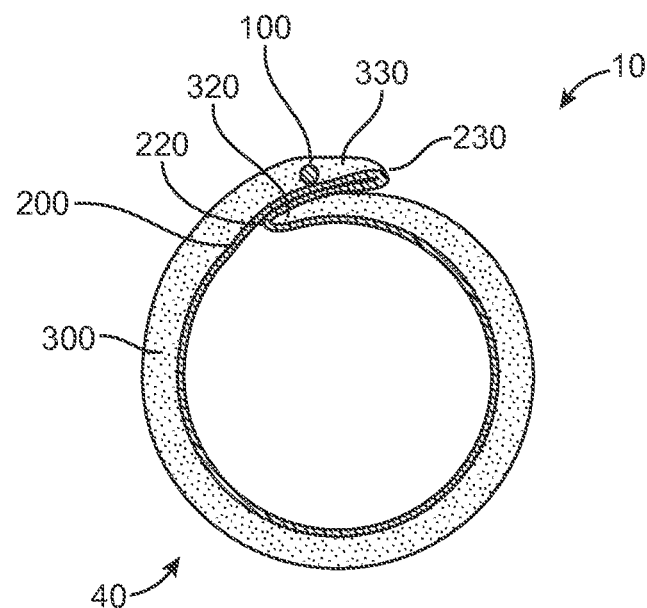
FIG. 8 is a sectional view of an elastic introducer according to an aspect of this disclosure.

Referring now to FIG. 7, elastic introducer 10 is shown in a collapsed configuration where wire structure 100 does not include a wire overlap region 114. In this aspect, second loop portions 122 extend slightly beyond inner fold 220 and inner edge 320.

Referring now to FIGS. 8-14, elastic introducer 10 is designed to allow for local expansion and subsequent recoil to reduce trauma to a patient's vessel. While introducing a transcatheter device, elastic introducer 10 can transition from a collapsed state 40 prior to accommodating transcatheter device 400, an expanded state 50 to accommodate transcatheter device 400, and a reduced state 60 after passage of transcatheter device 400. The diameter of elastic introducer 10 increases in expanded state 50 to accommodate transcatheter device 400. This increase in diameter is accomplished by first loop portions 112 and second loop portions 122 of wire structure 100 and inner edge 320 and outer edge 330 of jacket 300 diverging circumferentially to increase the effective diameter of elastic introducer 10. As elastic introducer 10 increases in diameter, inner fold 220 and outer fold 230 are flattened to allow liner gap portion 240 to span across jacket gap 340. Thus, liner gap portion 240 extends across jacket gap 340 and maintains a circumferentially continuous structure.

Arrow 410 shows the direction of travel of transcatheter device 400 through elastic introducer 10. Expanded state 50 of elastic introducer 10 is limited to the portion of elastic introducer 10 that surrounds transcatheter device 400. As transcatheter device 400 is moved distally in the direction of arrow 410, distal portions of elastic introducer 10 transition to expanded state 50 to accommodate transcatheter device 400. Furthermore, proximal portions of elastic introducer 10 transition to reduced state 60 following passage of transcatheter device 400.

After passage of transcatheter device 400, elastic introducer 10 recoils and reduces in diameter to reduced state 60, proximal to transcatheter device 400. The recoil and reduction in diameter is accomplished by the elasticity of wire structure 100. The elasticity of wire structure 100 allows first loop portions 112 and second loop portions 122 of wire structure 100 and inner edge 320 and outer edge 330 of jacket 300 to converge circumferentially and to reduce the effective diameter of elastic introducer 10. As elastic introducer 10 reduces in diameter, inner fold 220 and outer fold 230 are again utilized to allow outer edge 330 to partially cover the liner gap portion 240.

In one aspect, the diameter of elastic introducer 10 in the reduced state 60 is equal to the diameter of elastic introducer 10 in the collapsed state 40. In an alternate aspect, the diameter of elastic introducer 10 in the reduced state 60 is greater than the diameter of elastic introducer 10 in the collapsed state 40. In one aspect, elastic introducer 10 expands from a diameter of approximately 15 FR to approximately 19 FR. In an alternate aspect, elastic introducer 10 expands from a diameter of approximately 13 FR to approximately 18 FR.

In one aspect, elastic introducer 10 can be sized for a transcatheter heart valve procedure and can be used with a transcatheter heart valves and delivery system such as those described in U.S. Pat. No. 8,414,645; and U.S. Patent Publication Nos. 2006/0265056, 2007/0239266, 2007/0239269, and 2011/0251681, which are incorporated herein by reference in their entirety. For example, transcatheter device 400 can be an aortic valve prosthesis.

In alternate aspects, elastic introducer 10 can be sized for endoscopic procedures, procedures in the coronary vessels, or procedures in the peripheral vessels.

Figure 15:
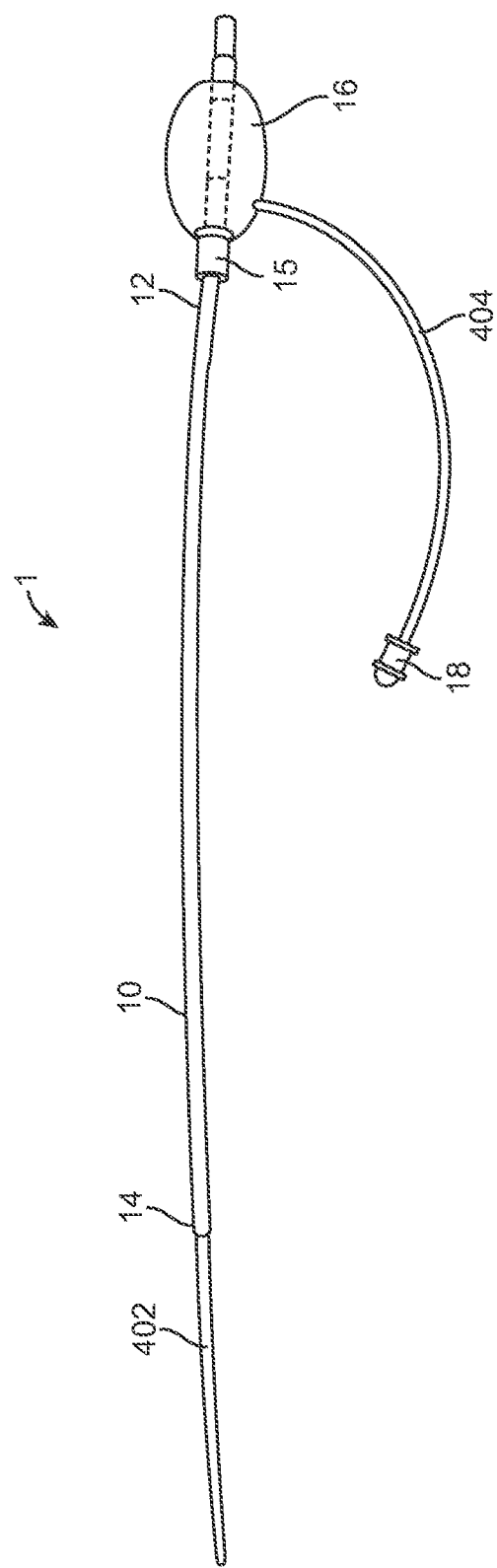
FIG. 15 is a top view of an introducer system according to an aspect of this disclosure.

Introducer system 1 is shown in FIG. 15. Introducer system 1 includes elastic introducer 10, a proximal end 12, a dilator 402, a flush tube 404, a proximal hub including a valve 16, and a Luer connector or stopcock 18. In one aspect, dilator 402 is 14.5 FR. In another aspect, proximal end 12 is non-expandable.

Figure 18:
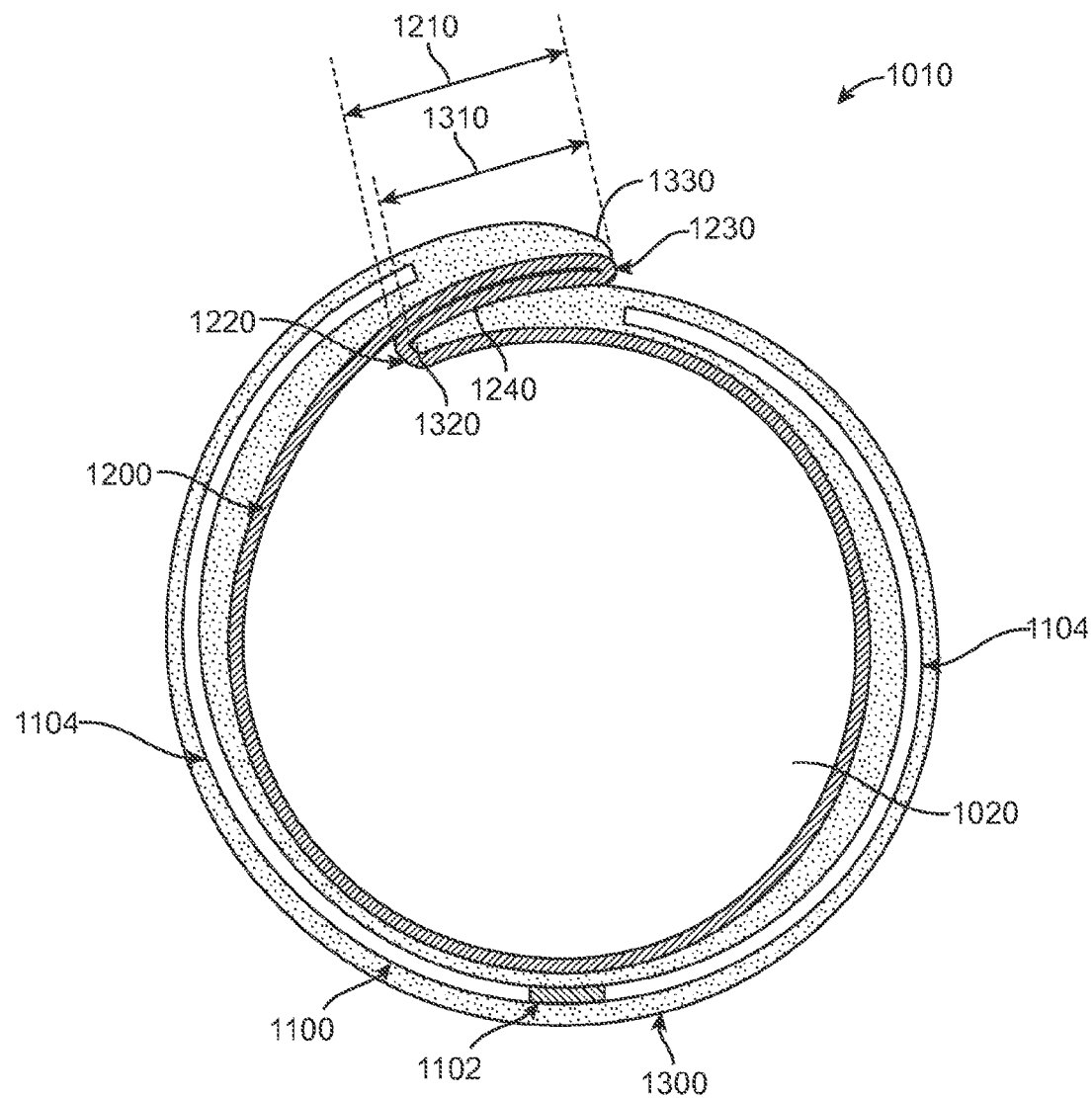
FIG. 18 is a sectional view of an elastic introducer according to an aspect of this disclosure.
Figure 19:
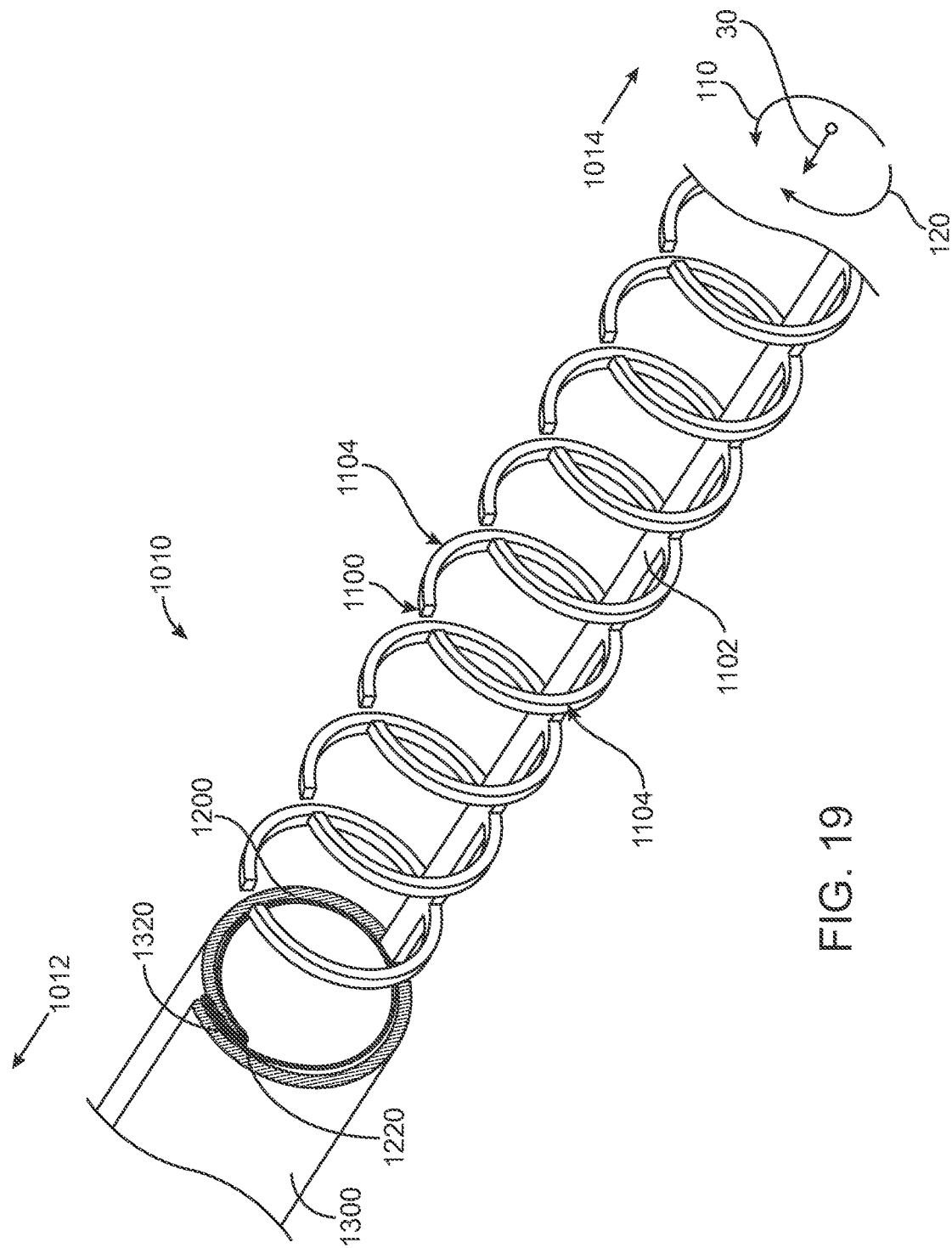
FIG. 19 is a perspective and cut away view of an elastic introducer according to an aspect of this disclosure.
Figure 36:
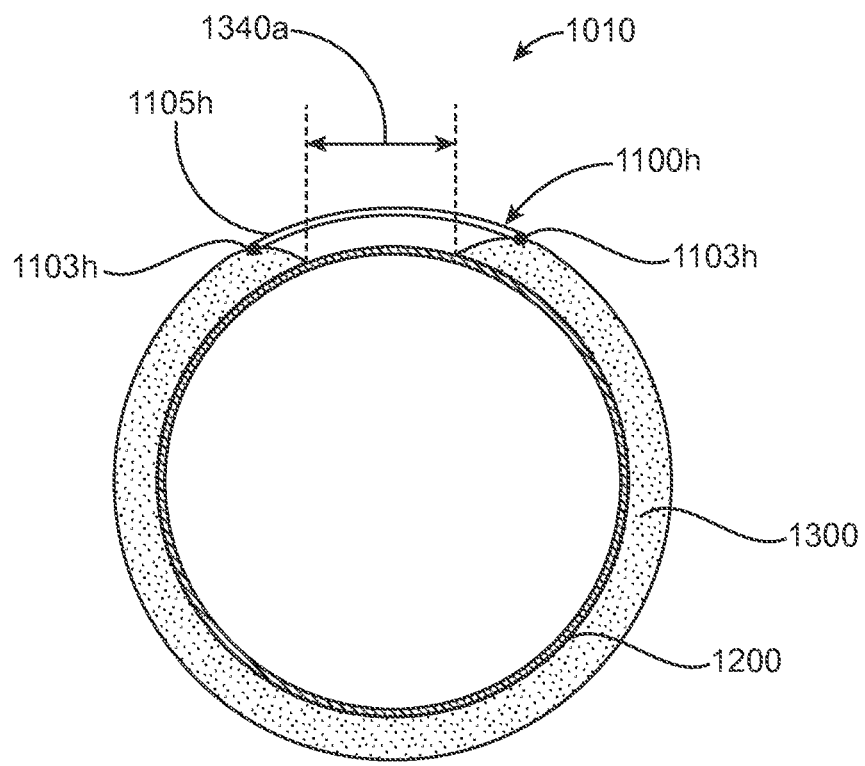
FIG. 36 is a sectional view of an elastic introducer according to an aspect of this disclosure.
Figure 37:
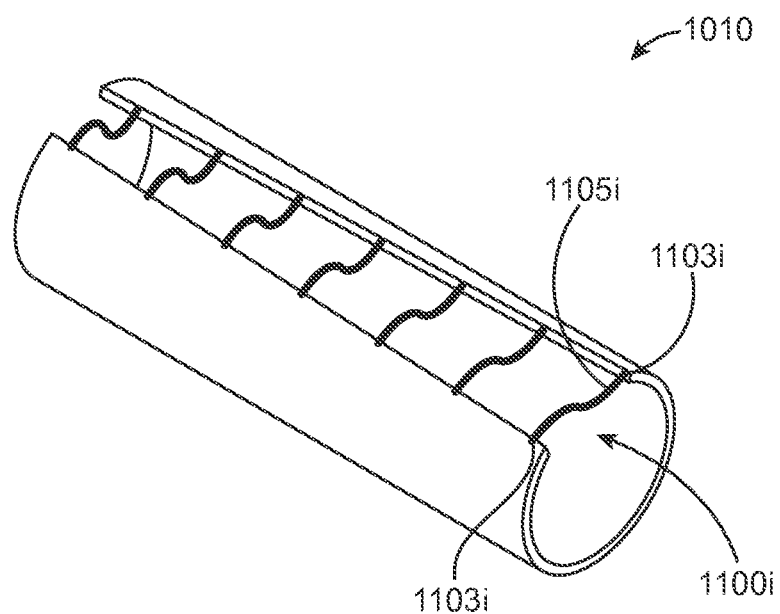
FIG. 37 is a perspective view of an elastic introducer frame according to an aspect of this disclosure.

Referring to FIGS. 18-19, elastic introducer 1010 has a proximal end 1012 and a distal end 1014. All of the features discussed above with respect to introducer system 1 and elastic introducer 10 are incorporated into the following description of elastic introducer 1010 and introducer system 1001. Like reference numbers indicate identical or functionally similar elements. Elastic introducer 1010 includes an elastic frame 1100, a liner 1200, and a jacket 1300. In one aspect, liner 1200 is circumferentially continuous and forms a lumen 1020. In this aspect, elastic frame 1100 and jacket 1300 are not circumferentially continuous and include a longitudinal gap visible in an expanded configuration. In a collapsed configuration, elastic introducer 1010 includes a liner overlap region 1210 and a jacket overlap region 1310. Liner overlap region 1210 includes liner gap portion 1240 defined by an inner fold 1220 and an outer fold 1230 of liner 1200. Liner gap portion 1240 can be at least partially covered by jacket 1300. In one aspect, liner 1200 extends around inner edge 1320 to form inner fold 1220. Jacket overlap region 1310 is defined by inner edge 1320 and outer edge 1330 of jacket 1300. In an expanded configuration, inner edge 1320 and outer edge 1330 are separated longitudinally to form a jacket gap 1340 (FIG. 36). In such a configuration, inner fold 1220 and outer fold 1230 are flattened to allow liner gap portion 1240 to extend across jacket gap 1340.

In one aspect, elastic frame 1100 is laminated between liner 1200 and jacket 1300. In an alternate aspect, elastic frame 1100 is embedded within jacket 1300. Elastic frame 1100 provides kink resistance for elastic introducer 1010 and also allows elastic introducer 1010 to actively recoil to a reduced diameter after passage of a transcatheter medical device through a portion of elastic introducer 1010.

FIGS. 18-39 show embodiments of elastic frame 1100. In one aspect, elastic frame 1100 includes spine 1102 and one or more projections 1104 connected along spine 1102. As shown, for example, in FIG. 20, elastic frame 1100, or portions thereof, can be stamped, etched, and/or cut from a flat sheet of material using techniques that are known in the art. Flat elastic frame 1100 can then be rolled, shaped, and heat set to form a tubular structure for use within elastic introducer 1010. If elastic frame 1100 is cut from a flat sheet of material, elastic frame 1100 may have a flattened or rectangular cross-section, however other shapes and/or cross-sections are acceptable. In another aspect, elastic frame 1100, or portions thereof, can be cut and/or etched from a tube of material using techniques that are known in the art. For example, elastic frame 1100 may be laser cut from a piece of material. Elastic frame 1100 may be cut or formed from a single piece of material or may be assembled from a number of different components and/or materials. For example, elastic frame 1100 may comprise nickel titanium, Nitinol, nickel-cobalt-chromium-molybdenum (MP35N), stainless steel, high spring temper steel, and/or any other metal or composite having elastic properties to permit extension and recoil of elastic introducer 10. In one aspect, following cutting, elastic frame 1100 may be processed further, for example, removal of sharp edges or burrs, wall thickness reduction, etc., which may be accomplished via filing, micro-blasting, acid-etching, electro-polishing, etc.

Spine 1102 provides axial stiffness along elastic introducer 1010. Projections 1104 permit bending of elastic introducer 1010 as it is passed through a patient's vasculature. Projections 1104 are non-circumferentially continuous and thus allow elastic introducer 1010 to locally expand to an expanded diameter to accommodate passage of a transcatheter medical device through elastic introducer 1010. Projections 1104 also maintain a radial force inward towards the center of elastic introducer 1010 so that elastic introducer 1010 can actively recoil to a reduced diameter after passage of the transcatheter medical device.

Figure 21:
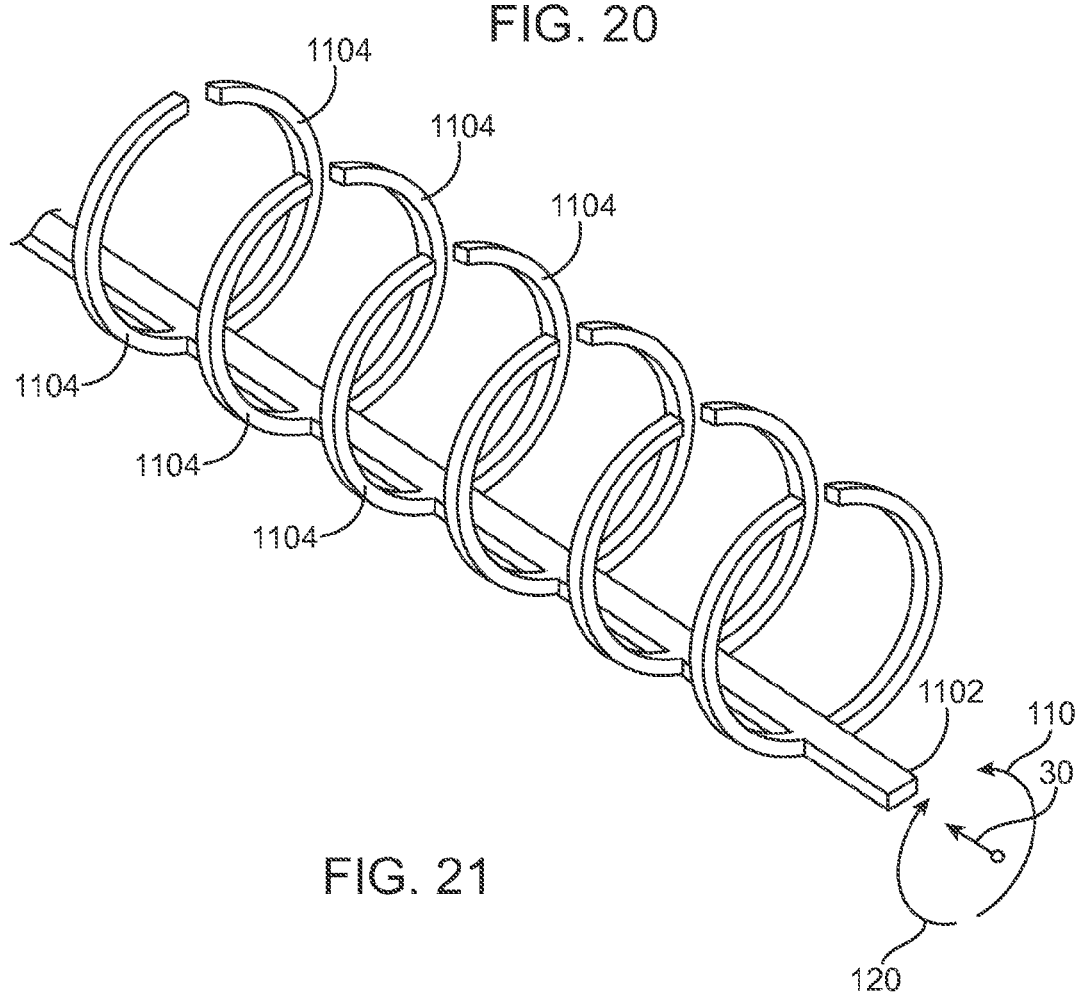
FIG. 21 is a perspective view of an elastic introducer frame according to an aspect of this disclosure.
Figure 22:
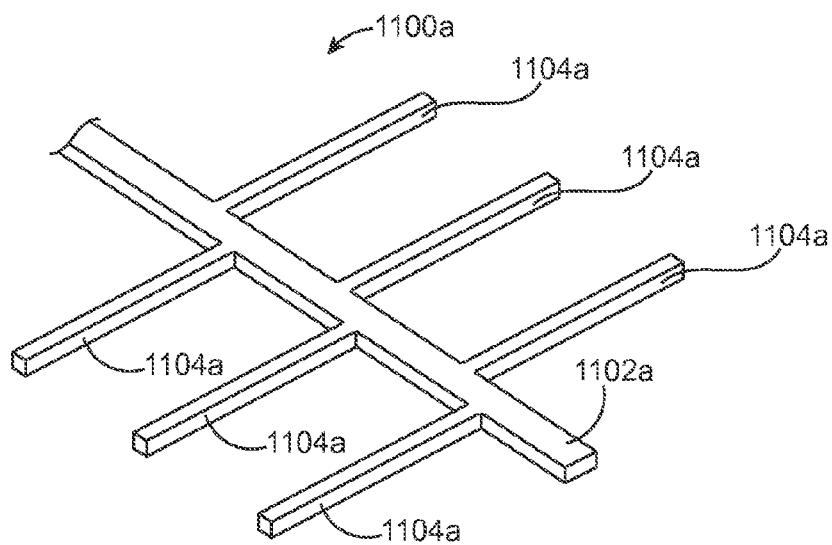
FIG. 22 is a perspective view of an elastic introducer frame according to an aspect of this disclosure.
Figure 23:
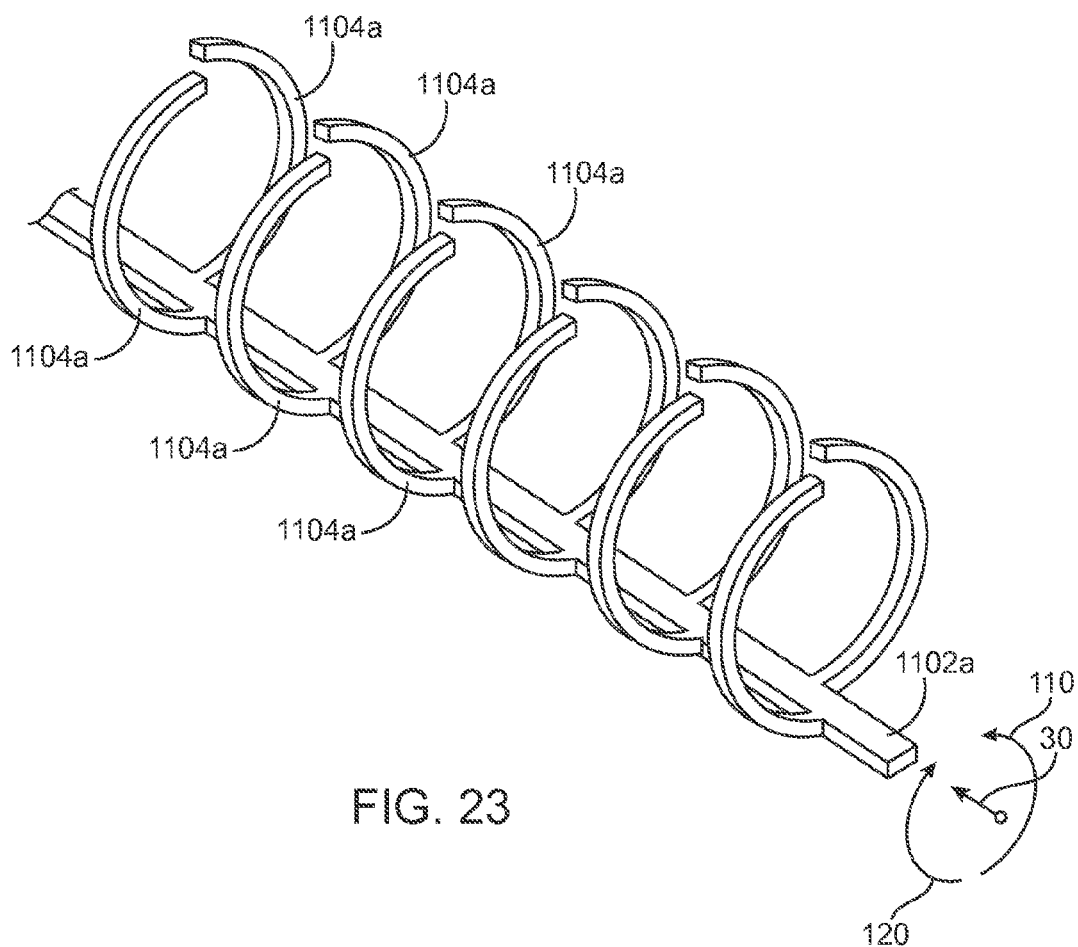
FIG. 23 is a perspective view of an elastic introducer frame according to an aspect of this disclosure.
Figure 24:
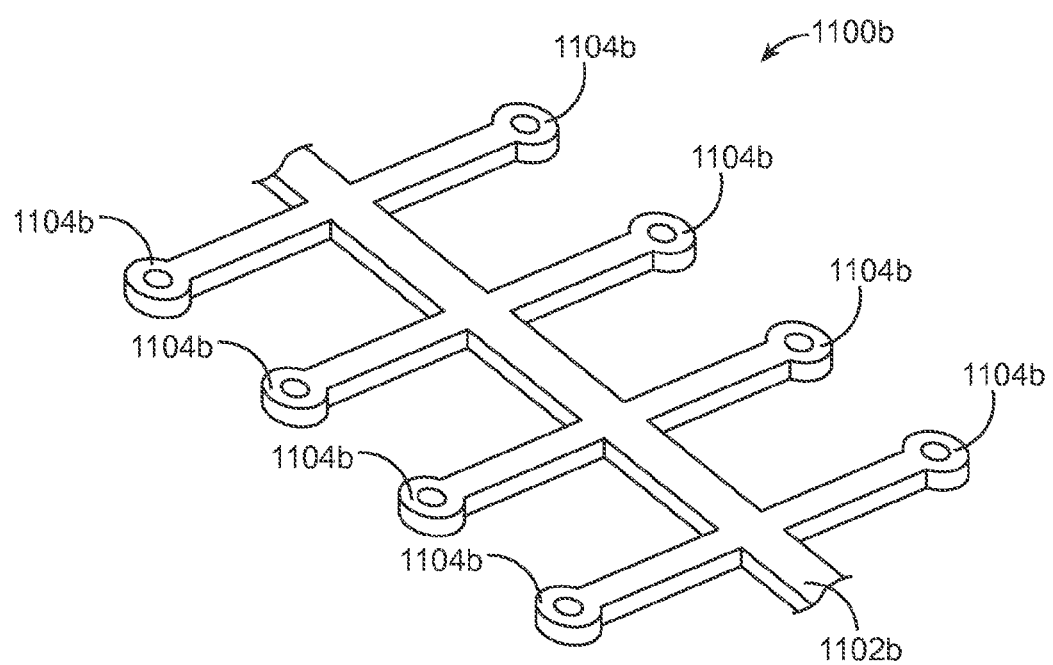
FIG. 24 is a perspective view of an elastic introducer frame according to an aspect of this disclosure.
Figure 25:
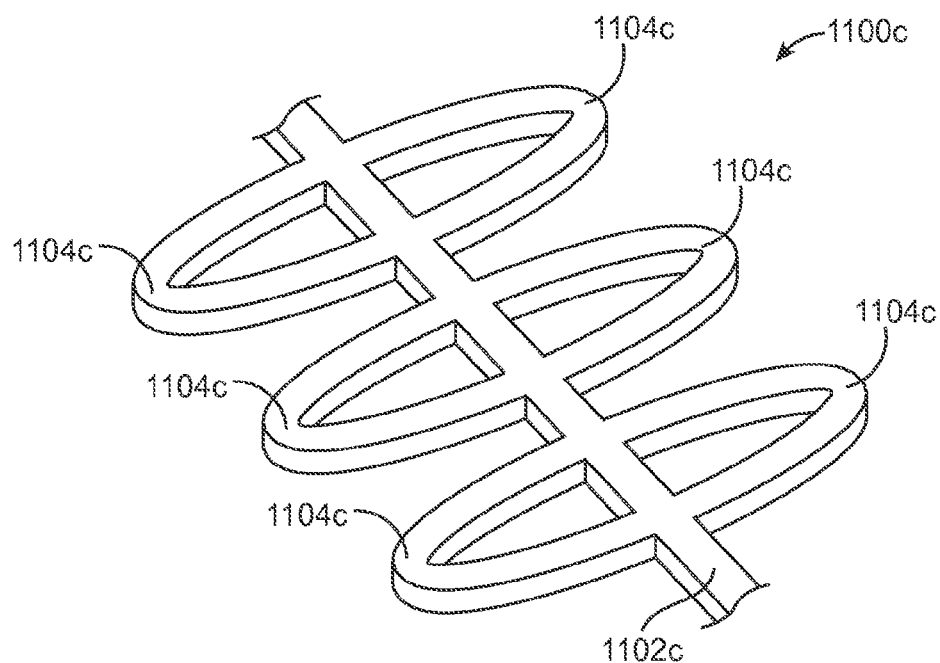
FIG. 25 is a perspective view of an elastic introducer frame according to an aspect of this disclosure.

Projections 1104 can extend from one or both edges of spine 1102. As shown in FIGS. 19 and 21, projections 1104 are curved about longitudinal axis 30 into a C-shape in a first radial direction 110 or a second radial direction 120. In a collapsed configuration, a portion of jacket 1300 overlaps in jacket overlap region 1310. In one aspect, the projections 1104 do not extend circumferentially into jacket overlap region 1310. In another aspect, projections 1104 extend into jacket overlap region 1310. In this aspect, when elastic introducer 1010 is in a collapsed configuration, projections 1104 extending in first radial direction 110 are positioned radially beneath the projections 1104 extending in second radial direction 120 within jacket overlap region 1310.

Figure 20:
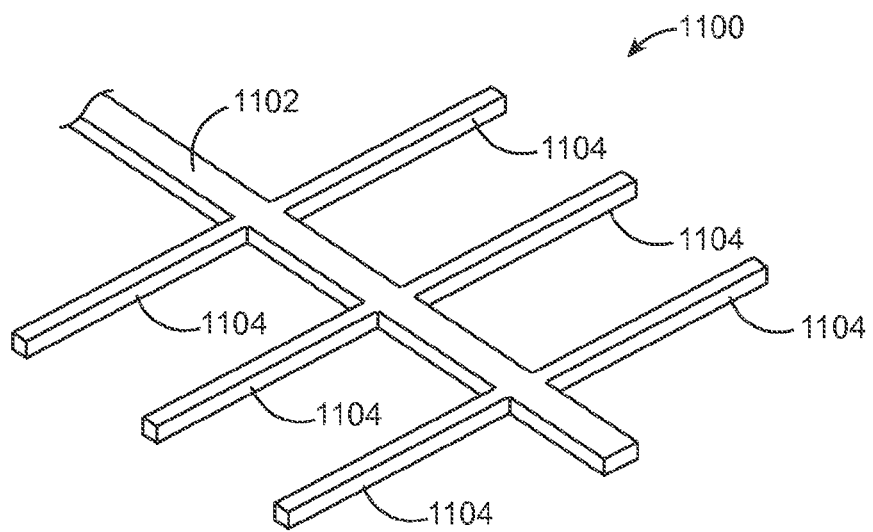
FIG. 20 is a perspective view of an elastic introducer frame according to an aspect of this disclosure.
Figure 31:
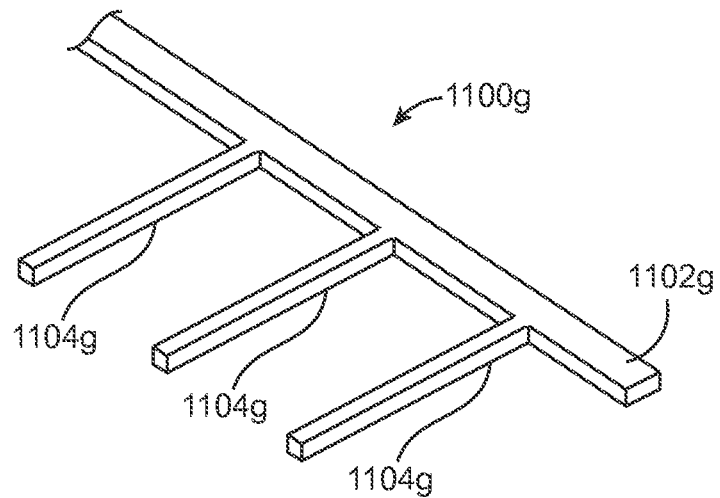
FIG. 31 is a perspective view of an elastic introducer frame according to an aspect of this disclosure.

The number, shape, and pattern of projections 1104 can affect expansion stress, flexibility, and bending compliance of elastic introducer 1010. FIGS. 19-33 show some of the possible patterns. As shown in FIGS. 20-21, a projection 1104 extending in first radial direction 110 and an opposing projection 1104 extending in second radial direction 120 can extend from the same axial location on spine 1102. In another embodiment, projections 1104*a* extending from opposite edges of spine 1102*b* can be offset. For example, a projection 1104*a* extending in first radial direction 110 and an opposing projection 1104*a* extending in second radial direction 120 can extend from different axial locations on spine 1102b. The offset of projections 1104a permits a smaller profile for elastic introducer 1010. In another aspect, projections 1104b can include a curved circular portion at one end. In a further embodiment, projections 1104c can be arched along spine 1102c. As shown in FIG. 31, all projections 1104g can extend from a single side of spine 1102g.

Figure 26:
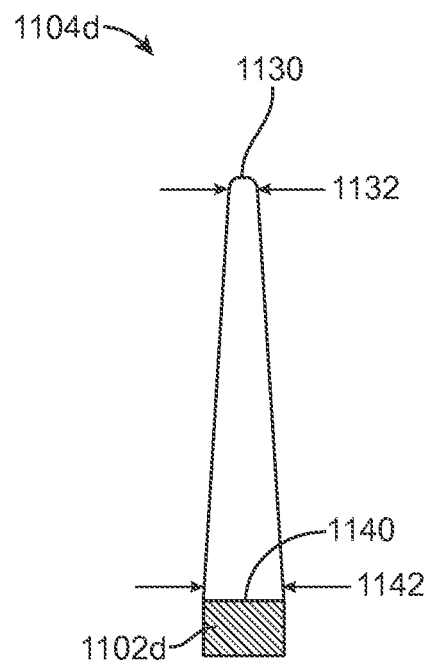
FIG. 26 is a side view of an elastic introducer frame projection according to an aspect of this disclosure.

As shown in FIG. 26, the thickness of a portion of projection 1104d can be modified so that projection 1104d is tapered in the radial direction. For example, projection 1104d can have a tip end 1130 with a tip end thickness 1132 and a spine end 1140 with a spine end thickness 1142. In one aspect, spine end thickness 1142 is greater than tip end thickness 1132, providing projection 1104d with a tapered profile. The tapered profile of projection 1104d permits an overall lower profile of elastic introducer 1010. In one embodiment, the size of spine end thickness 1142 and tip end thickness 1132 can each range from approximately 0.005 inches to approximately 0.015 inches.

Figure 27:
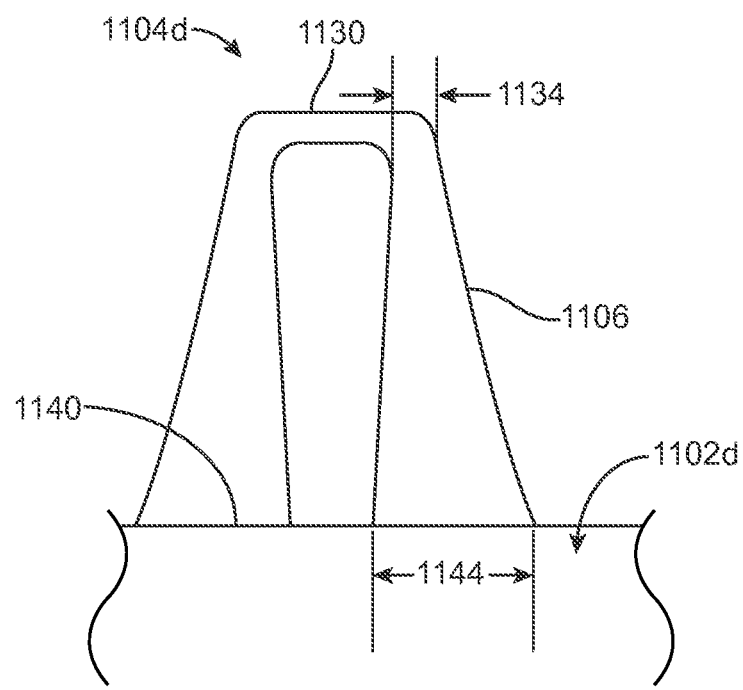
FIG. 27 is a front view of an elastic introducer frame projection according to an aspect of this disclosure.
Figure 28:
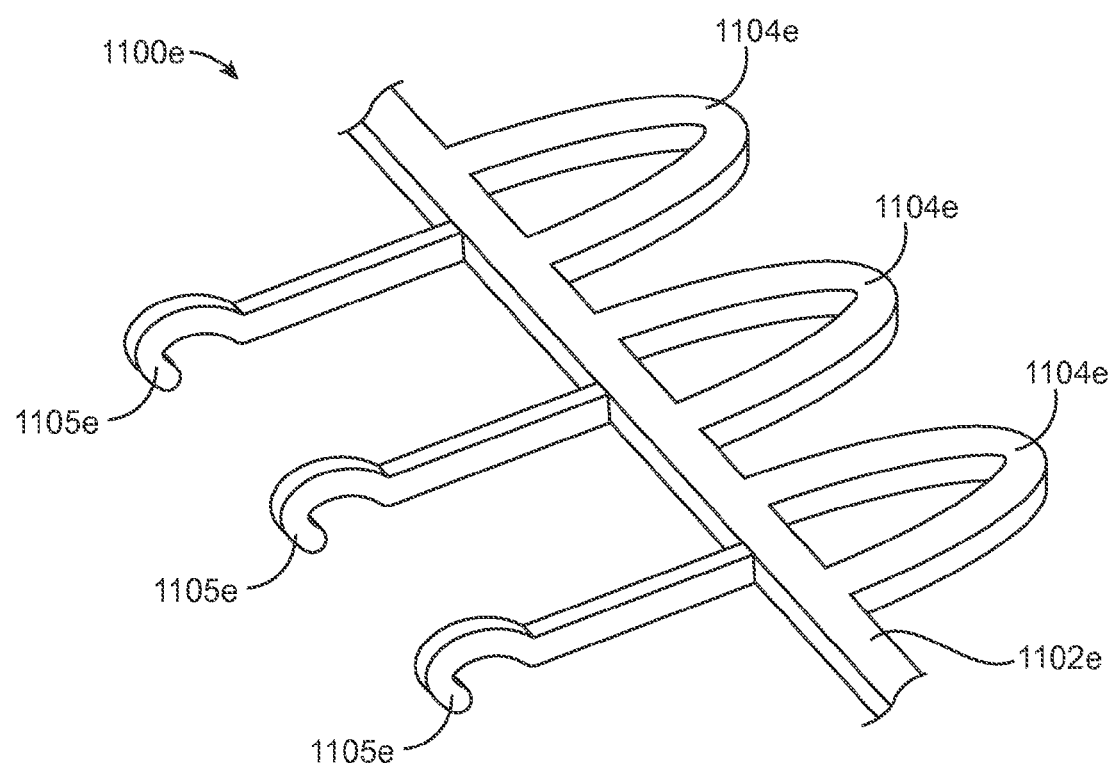
FIG. 28 is a perspective view of an elastic introducer frame according to an aspect of this disclosure.
Figure 29:
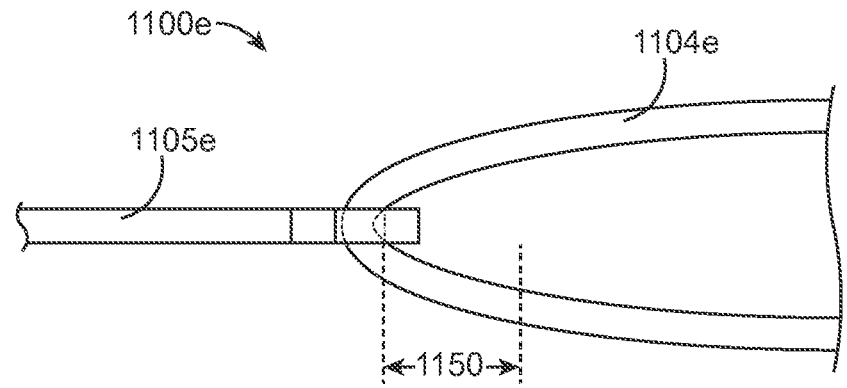
FIG. 29 is a top view of an elastic introducer frame according to an aspect of this disclosure.
Figure 30A:
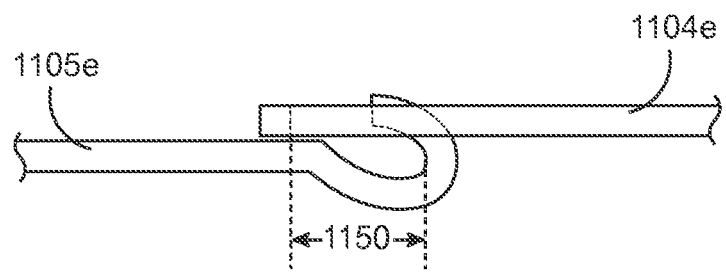
FIG. 30a is a side view of an elastic introducer frame according to an aspect of this disclosure.
Figure 30B:
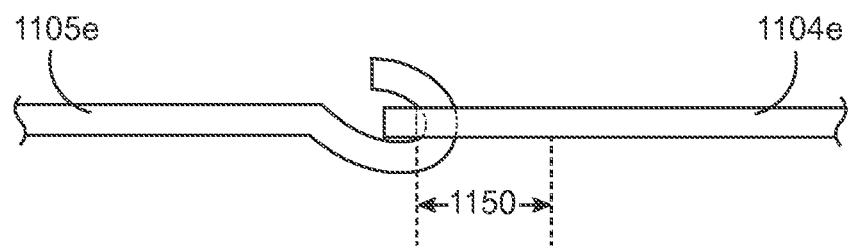
FIG. 30b is a side view of an elastic introducer frame according to an aspect of this disclosure.

In another embodiment shown in FIG. 27, the width of a portion of projection 1104d can be modified so that projection 1104d can be tapered in the axial direction. For example, projection strut 1106 on projection 1104d can have a spine end width 1144 and a tip end width 1134. In one aspect, spine end width 1144 is greater than tip end width 1134. In one embodiment, the size of spine end width 1144 and tip end end width 1134 can each range from approximately 0.005 inches to approximately 0.030 inches.

Referring now to FIGS. 28-30b, elastic frame 1100e can incorporate hook projections 1105e with eye projections 1104e to limit the maximum expansion of elastic frame 1100e and elastic introducer 1010. When formed in a tubular structure, each hook projection 1105e can engage with a respective eye projection 1104e to limit the expansion of elastic frame 1100e to expansion distance 1150. In one embodiment, expansion distance 1150 can range from approximately 10 French to approximately 22 French.

Figure 32:
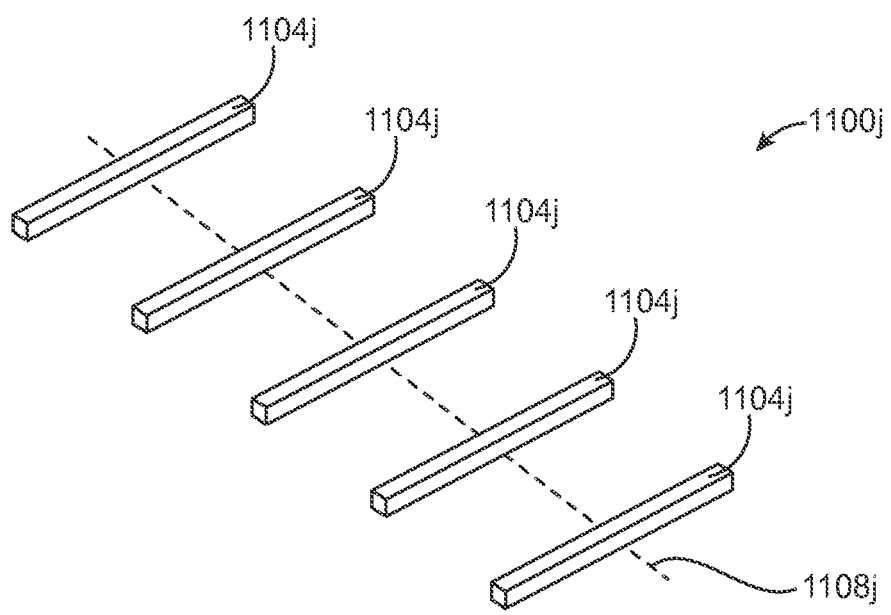
FIG. 32 is a perspective view of an elastic introducer frame according to an aspect of this disclosure.
Figure 33:
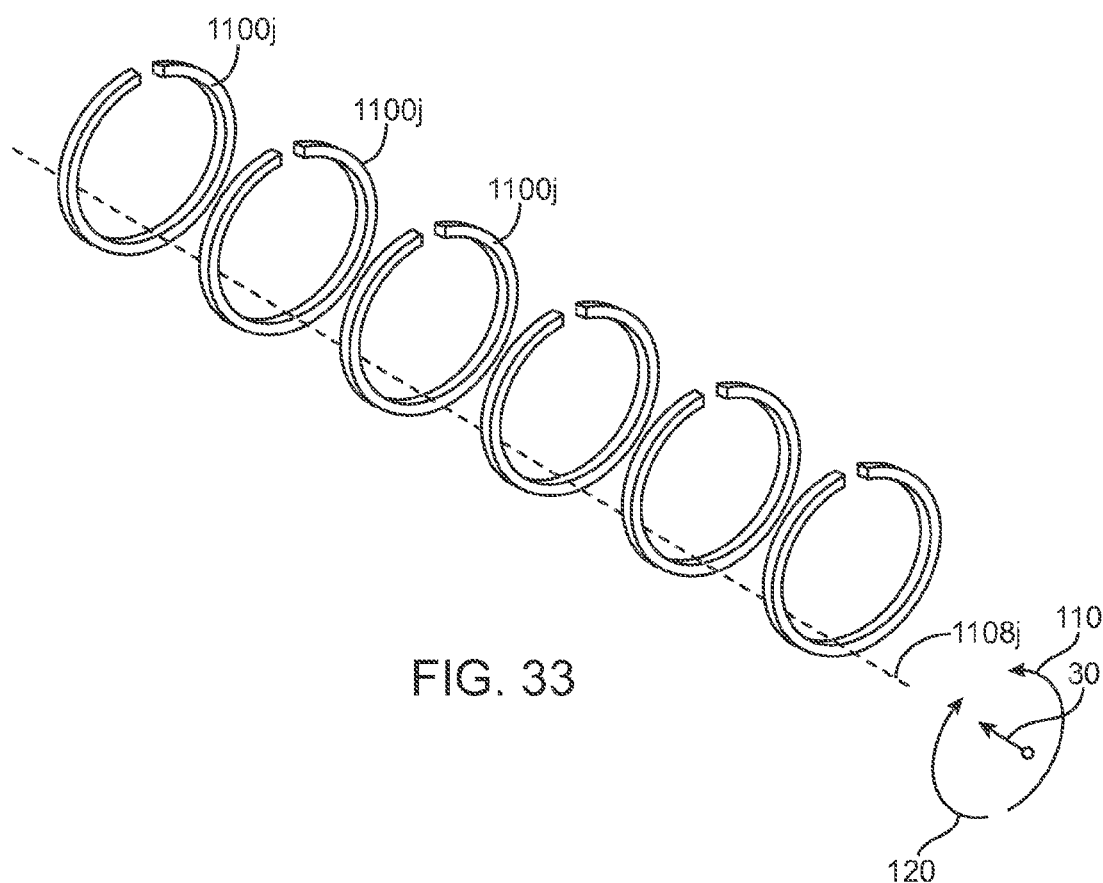
FIG. 33 is a perspective view of an elastic introducer frame according to an aspect of this disclosure.

Referring now to FIGS. 32-33, elastic frame 1100j can include one or more segmented projections 1104j spaced along common axis 1108j. Segmented projections 1104j are not joined by a common spine, but rather are connected through liner 1200 and/or jacket 1300 on elastic introducer 1010. Portions of each segmented projection are curved about longitudinal axis 30 into a C-shape in a first radial direction 110 or a second radial direction 120.

The axial spacing of projections 1104 along spine 1102 can be modified to alter the bending compliance and flexibility of elastic introducer 1010. For example, the axial spacing of projections 1104 along spine 1102 can be increased in areas of elastic introducer 1010 where additional flexibility is required. In one embodiment, the axial spacing between adjacent projections 1104 can range from approximately 1 mm to approximately 10 mm.

Figure 34:
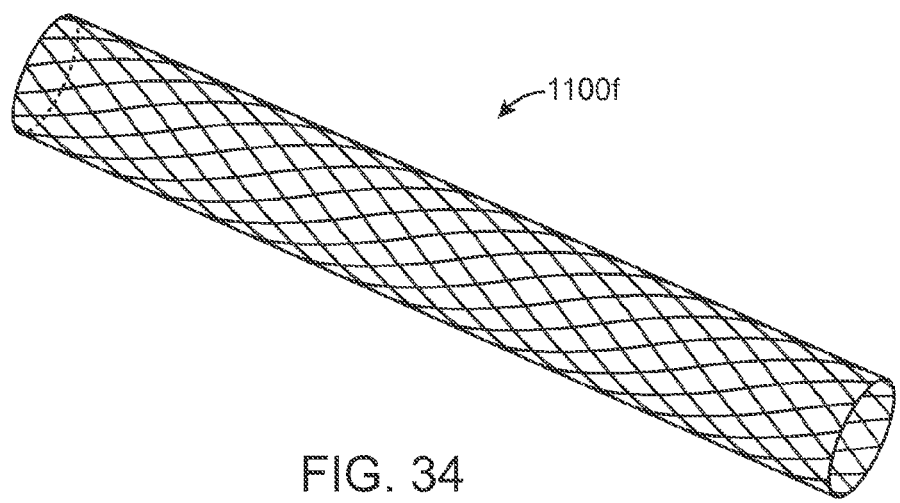
FIG. 34 is a perspective view of an elastic introducer frame according to an aspect of this disclosure.

Referring now to FIG. 34, elastic frame 1100f can be a stent-like laser cut tube having a plurality of diamond shaped cells that permit local expansion of elastic introducer 1010. In a further aspect, the shape of the cells and the stiffness of elastic frame 1100f can be modified along the length of elastic frame 1100f. In one aspect, elastic frame 1100f can have a proximal rigid portion designed to resist bending, a compliant mid-section designed to bend with and conform to a patient's anatomy, and a distal rigid portion designed to aid in valve retrieval.

Figure 35:
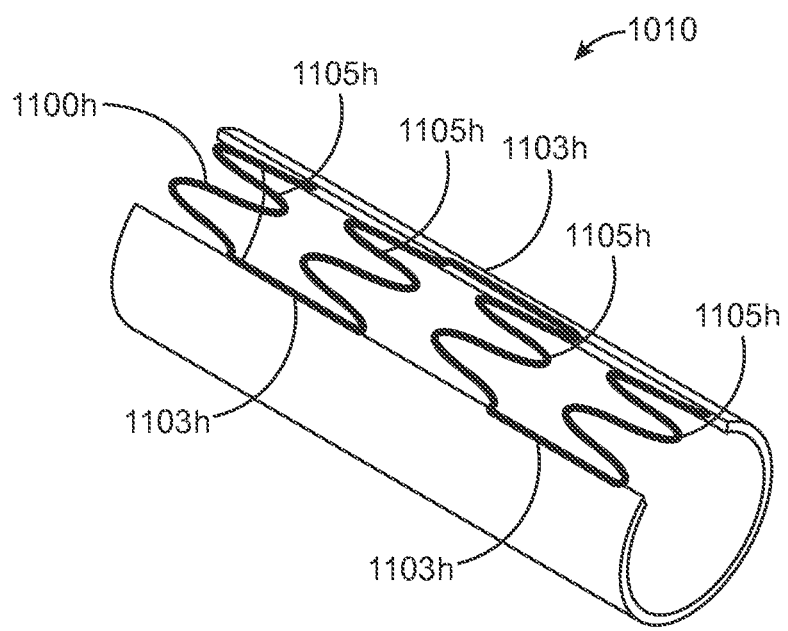
FIG. 35 is a perspective view of an elastic introducer frame according to an aspect of this disclosure.

In another embodiment, the elastic frame 1100 can be positioned across a fold or gap in elastic introducer 1010 to close jacket gap 1340. By reducing the amount of material used for elastic frame 1100, the design profile of elastic introducer 1010 can be minimized. As shown in FIGS. 35-36, elastic frame 1100h can have a continuous lace pattern across jacket gap 1340. Elastic frame 1100h includes an edge portion 1103h and a gap portion 1105h. Respective edge portions 1103h are anchored to inner edge 1320 and outer edge 1330 of jacket 1300 to provide a closing mechanism across jacket gap 1340. In another embodiment, elastic introducer 1010 can include one or more elastic frames 1100i axially spaced across jacket gap 1340. Elastic frames 1100i are distinct segments and are connected only through liner 1200 and/or jacket 1300 on elastic introducer 1010. Elastic frames 1100i can have an "N" or "Z" shape to permit expansion of introducer 1010. During expansion, elastic frames 1100i can straighten across jacket gap 1340 to locally increase the diameter of elastic introducer 1010. In one aspect, elastic frames 1100i can be laminated between liner 1200 and jacket 1300.

Figure 38:
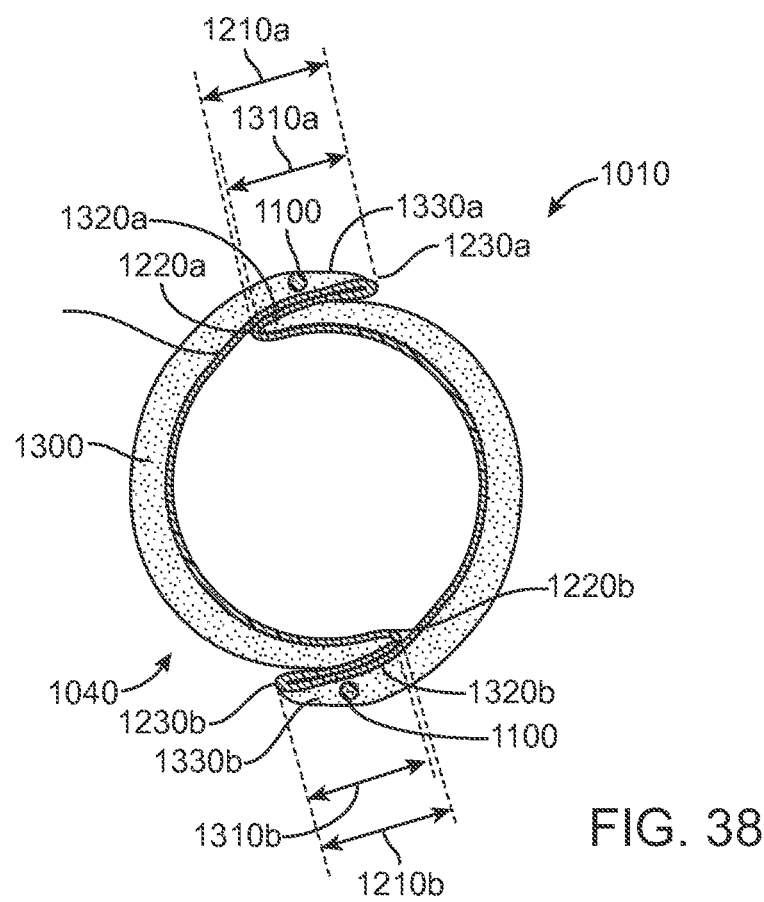
FIG. 38 is a sectional view of an elastic introducer according to an aspect of this disclosure.
Figure 39:
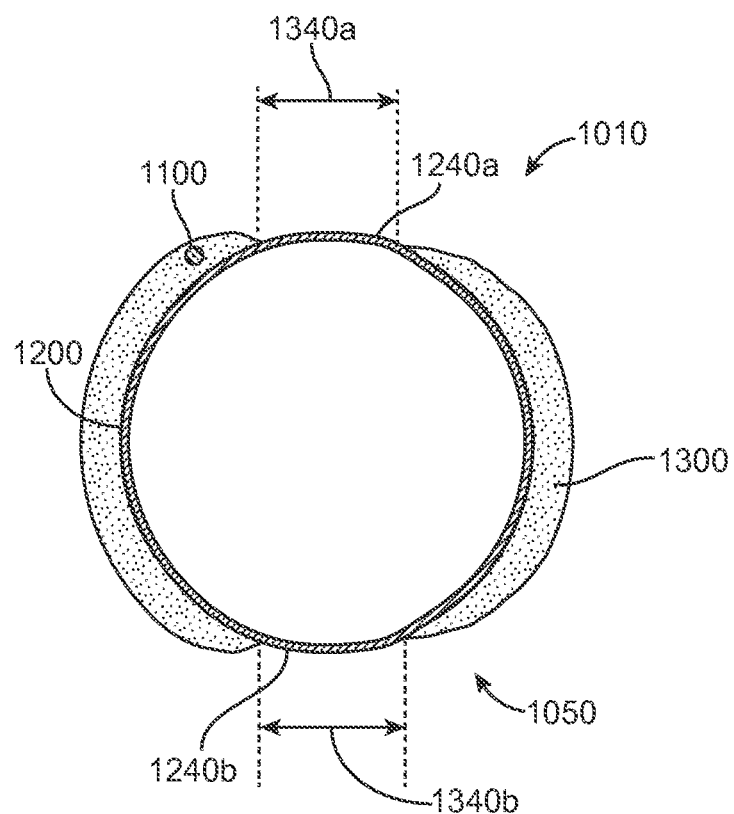
FIG. 39 is a sectional view of an elastic introducer according to an aspect of this disclosure.

In one aspect shown in FIGS. 38-39, elastic introducer 1010 can include multiple longitudinal gaps 1340a and 1340b. In this aspect, jacket 1300 can include at least two longitudinal gaps visible in an expanded configuration. In a collapsed configuration, elastic introducer 1010 includes two liner overlap regions 1210a, 1210b, and two jacket overlap regions 1310a, 1310b. Liner overlap regions 1210a, 1210b, include liner gap portions 1240a, 1240b, respectively defined by inner folds 1220a, 1220b, and outer folds 1230a, 1230b of liner 1200. Liner gap portions 1240a, 1240b, can be at least partially covered by jacket 1300. In one aspect, liner 1200 extends around inner edges 1320a, 1320b, to form inner folds 1220a, 1220b. Jacket overlap regions 1310a, 1310b, are defined by inner edges 1320a, 1320b and outer edges 1330a, 1330b of jacket 1300, respectively. In an expanded configuration, inner edges 1320a, 1320b, are separated longitudinally from outer edges 1330a, 1330b to form jacket gaps 1340a, 1340b. In the expanded configuration, inner folds 1220a, 1220b, and outer folds 1230a, 1230b are flattened to allow liner gap portions 1240a, 1240b to extend across jacket gaps 1340a, 1340b, respectively. In one aspect, each longitudinal gap 1340a and 1340b can include an elastic frame positioned across the gap, such as is discussed above with respect to FIGS. 35-36.

Because distal end 1014 of elastic introducer 1010 is expandable, jacket gap 1340 can fish-mouth, or open when elastic introducer 1010 traverses a bend in a patient's vasculature. As a result, inner fold 1220 and outer fold 1230 can flip at distal end 1014 causing a twist in jacket overlap region 1310. In addition, a user is required to twist elastic introducer 1010 on entry into the patient's vasculature to prevent opening of distal end 1014 from interaction with tissue.

Figure 40:
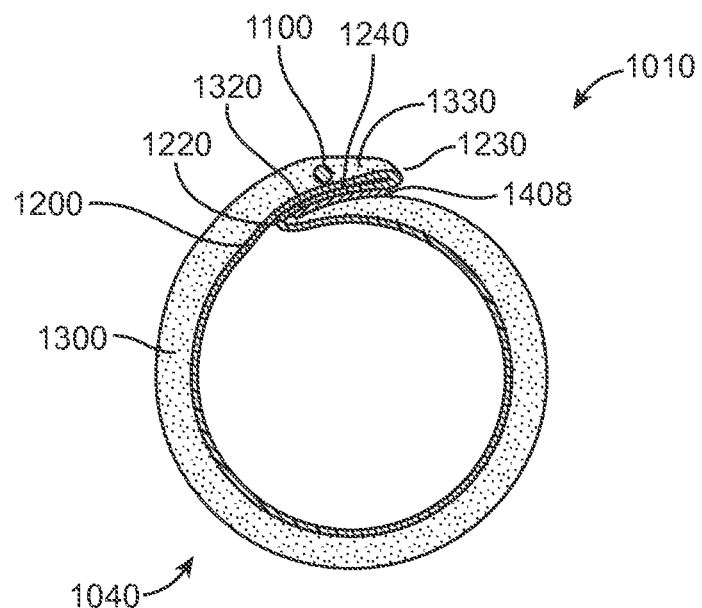
FIG. 40 is a sectional view of an elastic introducer according to an aspect of this disclosure.
Figure 41:
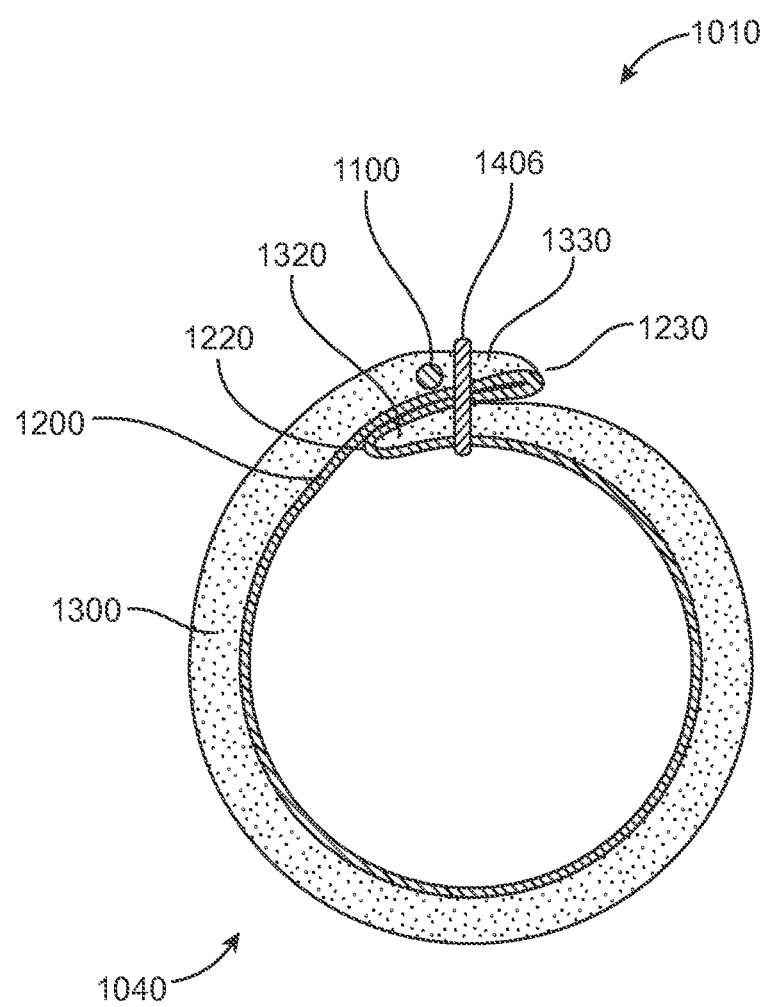
FIG. 41 is a sectional view of an elastic introducer according to an aspect of this disclosure.
Figure 42:
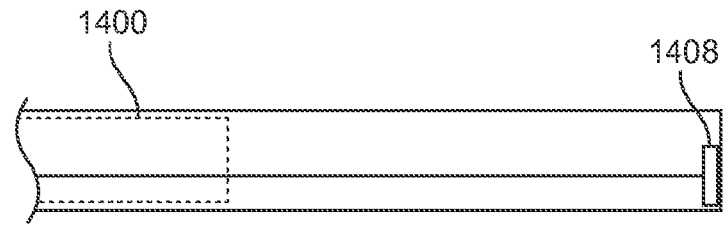
FIG. 42 is a top view of an elastic introducer according to an aspect of this disclosure.
Figure 43:
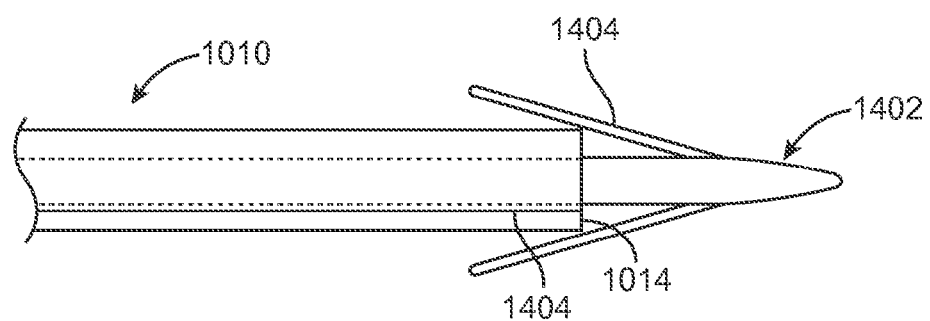
FIG. 43 is a top view of an elastic introducer system according to an aspect of this disclosure.
Figure 44:
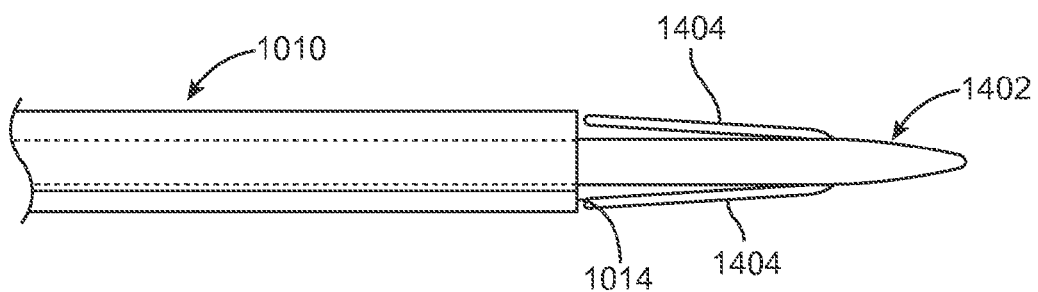
FIG. 44 is a top view of an elastic introducer system according to an aspect of this disclosure.
Figure 45:
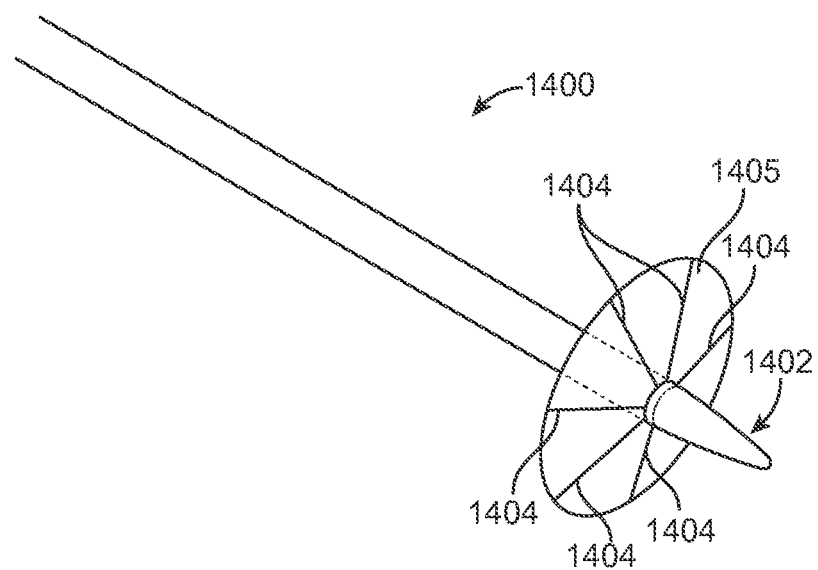
FIG. 45 is a perspective view of a dilator according to an aspect of this disclosure.
Figure 46:
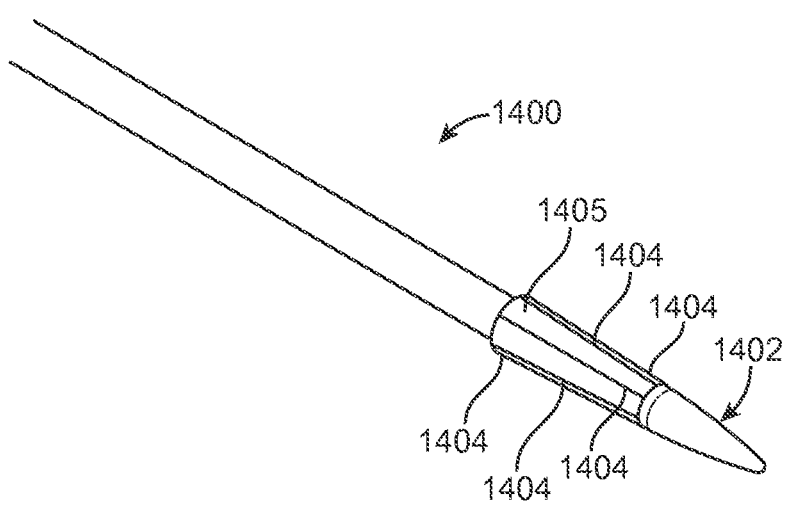
FIG. 46 is a perspective view of a dilator according to an aspect of this disclosure.
Figure 47:
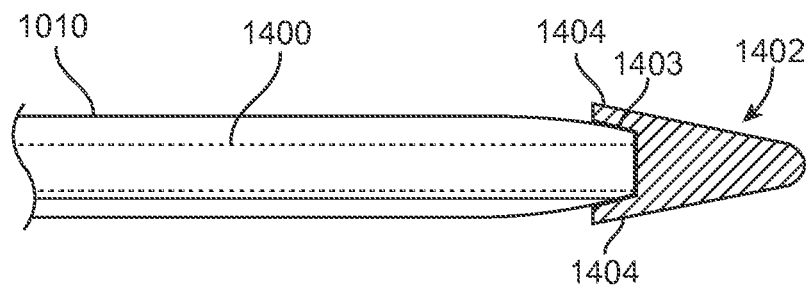
FIG. 47 is a partial sectional view of an elastic introducer system according to an aspect of this disclosure.
Figure 48:
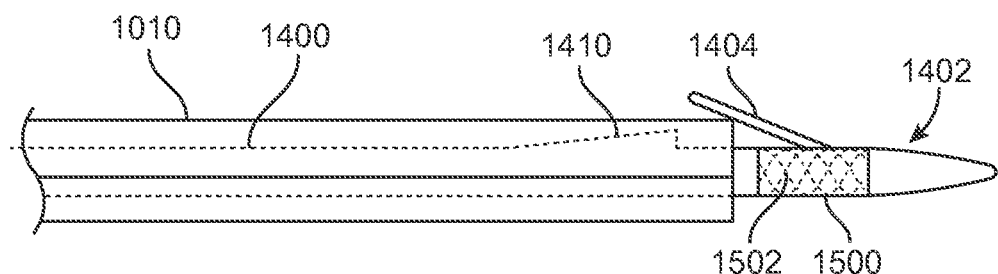
FIG. 48 is a top view of an elastic introducer system according to an aspect of this disclosure.
Figure 49:
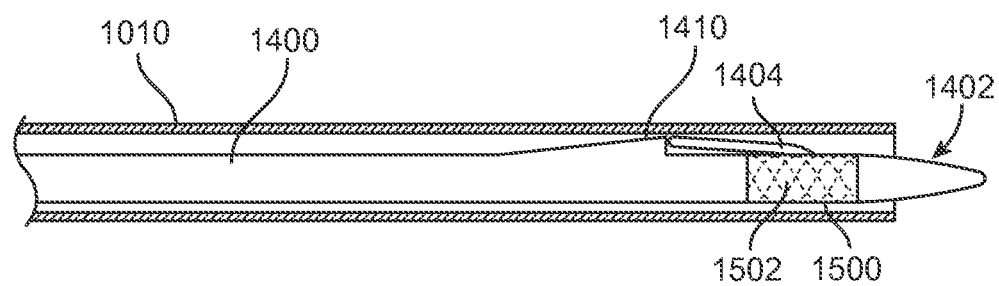
FIG. 49 is a top view of an elastic introducer system according to an aspect of this disclosure.

Referring now to FIGS. 40-42, diameter retention bond 1408 can be utilized to retain distal end 1014 in a collapsed or closed state. Diameter retention bond 1408 prevents distal end 1014 from opening during advancement of elastic introducer 1010 through the patient's vasculature. In one aspect, diameter retention bond 1408 seals and maintains inner fold 1220 and outer fold 1230 at distal end 1014 of elastic introducer 1010. Diameter retention bond 1408 can be positioned between jacket 1300 and liner gap portion 1240. In another aspect, diameter retention bond 1408 can be positioned between liner 1200 and liner gap portion 1240. In a further aspect, diameter retention bond 1408 can be positioned on jacket 1300 across outer edge 1330 and outer fold 1230, for example as shown in FIG. 42.

In another embodiment, diameter retention pin 1406 can be utilized to retain distal end 1014 in a collapsed or closed state. Diameter retention pin 1406 can extend through a portion of jacket 1340 and liner 1200 including liner gap portion 1240 and a portion of outer edge 1330 and a portion inner edge 1320. In another aspect, diameter retention pin 1406 can extend completely through liner gap portion 1240, outer edge 1330, and inner edge 1320 to retain distal end 1014 in a collapsed or closed state.

Diameter retention bond 1408 and diameter retention pin 1406 can be breakable and dissolvable upon passage of transcatheter device 400.

Referring now to FIGS. 43-49, dilator 1402 can include a diameter retention element 1404 to protect distal tip 1014 of elastic introducer 1010 and to retain distal end 1014 in a collapsed or closed state during advancement of elastic introducer 1010 through a patient's vasculature. During advancement, one or more diameter retention elements 1404 can extend around at least a portion of elastic introducer 1010 at distal end 1014. In one aspect, diameter retention element 1404 can extend across outer edge 1330 and outer fold 1230. Diameter retention element 1404 can be elastic and can collapse against dilator 1402 when dilator 1402 and diameter retention element 1404 are advanced beyond distal end 1014 of elastic introducer 1010. This allows dilator 1402 and diameter retention element 1404 to be pulled back through elastic introducer 1010.

In another embodiment, dilator 1402 can include a plurality of diameter retention elements 1404 supporting an introducer cover material 1405. Introducer cover material 1405 can be a biocompatible material and can cover the entire distal end 1014 of elastic introducer 1010.

In another embodiment, a dilator 1402 can include a recess 1403 formed by diameter retention elements 1404. During insertion, distal end 1014 of elastic introducer 1010 can be positioned within recessed 1403 of dilator 1402. In this aspect, diameter retention element 1404 can be movable by a retraction mechanism in hub 1015. The retraction mechanism can pull diameter retention elements 1404 against the outer surface of dilator 1402 to permit dilator 1402 and diameter retention elements 1404 to be pulled back through elastic introducer 1010.

In a further embodiment, dilator 1402 can include a device delivery capsule 1500 to retain a prosthetic device 1502. Diameter retention element 1404 can be positioned on delivery capsule 1500 and distal end 1014 of elastic introducer can be positioned under diameter retention element 1404. In this aspect, elastic introducer 1010 can be used as an inline sheath to advance elastic introducer 1010 and prosthetic device 1502 through a patient's vasculature. Introducers used as an inline sheath are discussed in U.S. Patent Publication Nos. 2011/208296, 2006/0206192, and U.S. application Ser. No. 13/914,802, which are incorporated herein by reference in their entirety. Diameter retention element 1404 can prevent distal end 1014 from opening and traveling over delivery capsule 1500 during use as an inline sheath. In a further aspect, dilator 1402 can include a ramp 1410 axially positioned proximal to diameter retention element 1404. Ramp 1410 lifts the edge of distal end 1014 as it approaches diameter retention element 1404 when dilator 1402 is passed back through elastic introducer 1010. Ramp 1410 can thus reduce the risk of diameter retention element 1404 snagging on distal end 1014.

Figure 50:
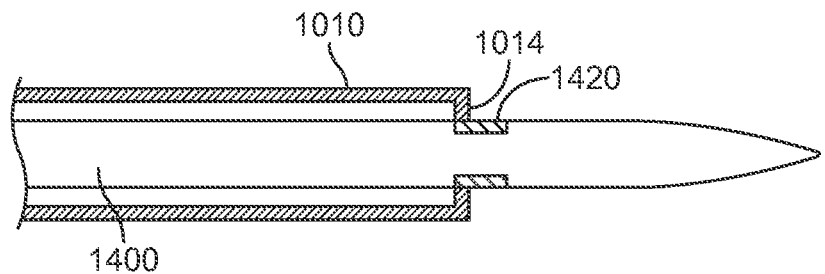
FIG. 50 is a partial sectional view of an elastic introducer system according to an aspect of this disclosure.
Figure 51:
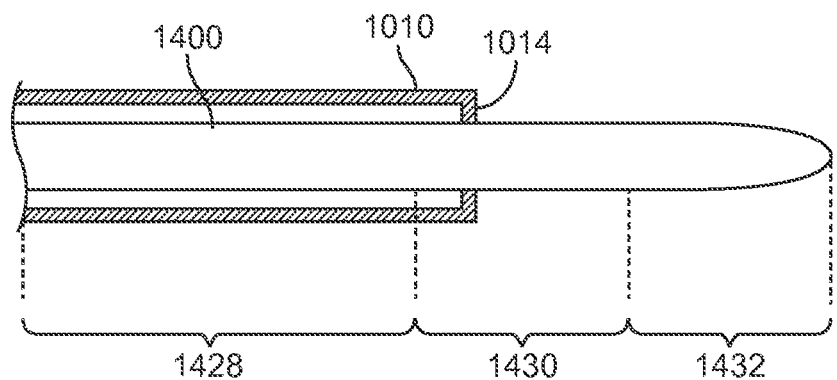
FIG. 51 is a partial sectional view of an elastic introducer system according to an aspect of this disclosure.
Figure 52:
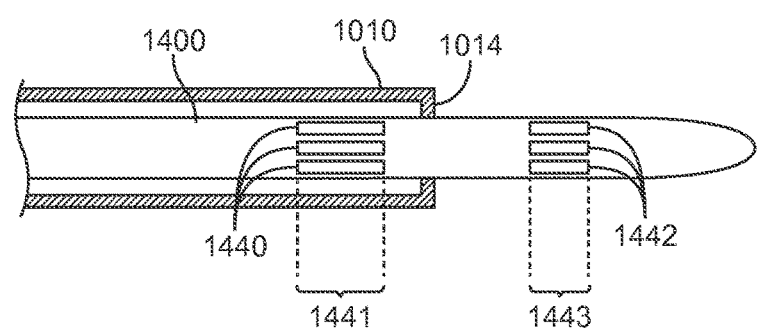
FIG. 52 is a partial sectional view of an elastic introducer system according to an aspect of this disclosure.

Referring now to FIGS. 50-52, in one embodiment, dilator 1402 can include a rigid section 1420 to prevent flexion of dilator 1402 at this section. Placing distal end 1014 of elastic introducer 1010 at rigid section 1420 can help to maintain distal end 1014 in a collapsed or closed state during advancement of elastic introducer 1010 through a patient's vasculature. Rigid section 1420 can be formed by placing additional material in a band-like structure on dilator 1402 or by using a higher durometer material in the region of rigid section 1420.

In another embodiment, dilator 1402 can include a proximal flexible section 1428 and/or a distal flexible section 1432 to induce bending of dilator 1402 in these sections. Placing distal end 1014 of elastic introducer 1010 in section 1430 at an axial location distal to proximal flexible section 1428 and proximal to distal flexible section 1432 can help to maintain distal end 1014 in a collapsed or closed state during advancement of elastic introducer 1010 through a patient's vasculature. Proximal flexible section 1428 and distal flexible section 1432 can be formed by using a lower durometer material in the region of the respective flexible sections.

In another embodiment, dilator 1420 can include one or more cuts 1440 around the outer surface of the dilator 1402 in the region of proximal flexible section 1441. And, dilator 1420 can include one or more cuts 1442 around the outer surface of dilator 1402 in the region of distal flexible section 1443. As with proximal flexible section 1428 and distal flexible section 1432, proximal flexible section 1441 and distal flexible section 1443 induce bending of dilator 1402 in these sections. Placing distal end 1014 of elastic introducer 1010 in a section at an axial location distal to proximal flexible section 1441 and proximal to distal flexible section 1443 can help to maintain distal end 1014 in a collapsed or closed state during advancement of elastic introducer 1010 through a patient's vasculature.

The foregoing description has been presented for purposes of illustration and enablement, and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. An elastic surgical access device comprising:
   a circumferentially continuous layer of a biocompatible material, the circumferentially continuous layer having an overlap region with at least one fold when the elastic surgical access device is in a collapsed configuration;
   an elastic frame; and
   a non-circumferentially continuous layer of a biocompatible material connected to the elastic frame and to the circumferentially continuous layer, the non-circumferentially continuous layer having an overlap region when the elastic surgical access device is in the collapsed configuration and a longitudinal gap when the elastic surgical access device is in an expanded configuration,
   wherein the respective overlap regions of the circumferentially continuous layer and the non-circumferentially continuous layer are substantially co-extensive when the elastic surgical access device is in the collapsed configuration, and
   wherein the at least one fold of the overlap region of the circumferentially continuous layer flattens to extend across the longitudinal gap of the non-circumferentially continuous layer when the elastic surgical access device is in the expanded configuration.

2. The elastic surgical access device of claim 1, wherein the elastic frame is a wire structure that is curved to form a C-shape in a radial direction.

3. The elastic surgical access device of claim 2, wherein the wire structure has a rectangular cross section.

4. The elastic surgical access device of claim 1, wherein the elastic frame extends along a length of the elastic surgical access device.

5. The elastic surgical access device of claim 4, wherein a stiffness of the elastic frame varies along the length of the elastic surgical access device.

6. The elastic surgical access device of claim 4, wherein the elastic frame includes a spine and a plurality of projections extending from the spine, the plurality of projections being axially spaced apart along the length of the elastic surgical access device.

7. The elastic surgical access device of claim 6, wherein each of the plurality of projections is curved to form a C-shape in a radial direction.

8. The elastic surgical access device of claim 6, wherein each of the spine and each of the plurality of projections has a rectangular cross section.

9. The elastic surgical access device of claim 1, wherein the elastic frame has a non-uniform geometry along its length.

10. The elastic surgical access device of claim 9, wherein a thickness of the elastic frame varies along its length.

11. The elastic surgical access device of claim 9, wherein a width of the elastic frame varies along its length.

12. The elastic surgical access device of claim 1, wherein the circumferentially continuous layer has a second overlap region with at least one fold when the elastic surgical access device is in the collapsed configuration and the non-circumferentially continuous layer has a second longitudinal gap when the elastic surgical access device is in the expanded configuration, wherein the at least one fold of the second overlap region of the circumferentially continuous layer flattens to extend across the second longitudinal gap of the non-circumferentially continuous layer when the elastic surgical access device is in the expanded configuration.

13. The elastic surgical access device of claim 1, wherein the elastic frame is a laser cut tube having a plurality of diamond shaped cells.

14. An elastic surgical access device comprising:
a circumferentially continuous layer of a biocompatible material, the circumferentially continuous layer having an overlap region with at least one fold when the elastic surgical access device is in a collapsed configuration;
an elastic frame that includes a spine and a plurality of projections extending from the spine that are curved to form a C-shape in a radial direction, the plurality of projections being axially spaced apart along the length of the elastic surgical access device; and
a non-circumferentially continuous layer of a biocompatible material connected to the elastic frame and to the circumferentially continuous layer, the non-circumferentially continuous layer having a longitudinal gap when the elastic surgical access device is in an expanded configuration, wherein the at least one fold of the overlap region of the circumferentially continuous layer flattens to extend across the longitudinal gap of the non-circumferentially continuous layer when the elastic surgical access device is in the expanded configuration, and
wherein each of the plurality of projections includes a hook projection at a first end of the C-shape and an eye projection at a second end of the C-shape, each hook projection configured to engage a respective eye projection to limit expansion of the elastic surgical access device.

15. A locally expandable surgical access device comprising:
a non-circumferentially continuous layer of a biocompatible material including a longitudinal gap along a length of the locally expandable surgical access device;
a circumferentially continuous layer of a biocompatible material connected to the non-circumferentially continuous layer; and
an elastic frame extending only across the longitudinal gap and connected to the non-circumferentially continuous layer on each side of the longitudinal gap, wherein the elastic frame includes a plurality of wavy segments that are axially spaced apart and are configured to permit expansion of the locally expandable surgical access device from a collapsed configuration to an expanded configuration.

16. The locally expandable surgical access device of claim 15, wherein the longitudinal gap extends between a first edge of the non-circumferentially continuous layer and a second edge of the non-circumferentially continuous layer, and
wherein the plurality of wavy segments of the elastic frame are formed from a continuous structure having a first edge portion that is attached to the first edge of the non-circumferentially continuous layer and a second edge portion that is attached to the second edge of the non-circumferentially continuous layer.

17. The locally expandable surgical access device of claim 15, wherein the circumferentially continuous layer has an overlap region with at least one fold when the locally expandable surgical access device is in a collapsed configuration and the at least one fold of the overlap region of the circumferentially continuous layer flattens to extend across the longitudinal gap of the non-circumferentially continuous layer when the locally expandable surgical access device is in an expanded configuration, and wherein the elastic frame is configured to maintain the locally expandable surgical access device in the collapsed configuration.

18. The locally expandable surgical access device of claim 15, wherein the longitudinal gap extends between a first edge of the non-circumferentially continuous layer and a second edge of the non-circumferentially continuous layer and wherein each of the plurality of wavy segments of the elastic frame is a distinct structure having a first end that is attached to the first edge of the non-circumferentially continuous layer and a second end that is attached to the second edge of the non-circumferentially continuous layer.

19. The locally expandable surgical access device of claim 18, wherein each of the plurality of wavy segments straighten when the locally expandable surgical access device is in the expanded configuration.

20. An elastic surgical access device comprising:
a circumferentially continuous layer of a biocompatible material, the circumferentially continuous layer having an overlap region with at least one fold when the elastic surgical access device is in a collapsed configuration;
a non-circumferentially continuous layer of a biocompatible material connected to the circumferentially continuous layer, the non-circumferentially continuous layer having a longitudinal gap when the elastic surgical access device is in an expanded configuration, wherein the at least one fold of the overlap region of the circumferentially continuous layer flattens to extend across the longitudinal gap of the non-circumferentially continuous layer when the elastic surgical access device is in the expanded configuration; and a segmented elastic frame disposed between the circumferentially continuous layer and the non-circumferentially continuous layer, the segmented elastic frame including a plurality of distinct projections, not joined to each other, that are axially spaced apart along a length of the elastic surgical access device.

* * * * *